US012691304B2

(12) United States Patent
Puleo et al.

(10) Patent No.: US 12,691,304 B2
(45) Date of Patent: Jul. 28, 2026

(54) NEUROMODULATION ENERGY APPLICATION TECHNIQUES

(71) Applicant: GE Precision Healthcare LLC, Waukesha, WI (US)

(72) Inventors: Christopher Michael Puleo, Niskayuna, NY (US); Yang Zhao, Schenectady, NY (US); Kirk Dennis Wallace, Schenectady, NY (US); Ying Fan, Schenectady, NY (US); Jeffrey Michael Ashe, Gloversville, NY (US); David Andrew Shoudy, Niskayuna, NY (US)

(73) Assignee: GE Precision Healthcare LLC, Waukesha, WI (US)

( * ) Notice: Subject to any disclaimer, the term of this patent is extended or adjusted under 35 U.S.C. 154(b) by 24 days.

(21) Appl. No.: 18/587,341

(22) Filed: Feb. 26, 2024

(65) Prior Publication Data

US 2024/0189629 A1     Jun. 13, 2024

Related U.S. Application Data

(63) Continuation of application No. 17/572,383, filed on Jan. 10, 2022, now Pat. No. 11,911,634, which is a
(Continued)

(51) Int. Cl.
| | |
|---|---|
| *A61N 7/00* | (2006.01) |
| *A61B 8/00* | (2006.01) |
| *A61B 90/00* | (2016.01) |

(52) U.S. Cl.
CPC .............. *A61N 7/00* (2013.01); *A61B 8/4245* (2013.01); *A61B 8/4254* (2013.01); *A61B 90/37* (2016.02);
(Continued)

(58) Field of Classification Search
CPC .............. A61N 7/00; A61N 2007/0026; A61N 2007/0052; A61N 2007/003;
(Continued)

(56) References Cited

U.S. PATENT DOCUMENTS

| | | |
|---|---|---|
| 5,413,550 A | 5/1995 | Castel |
| 6,611,715 B1 | 8/2003 | Boveja et al. |

(Continued)

FOREIGN PATENT DOCUMENTS

| | | |
|---|---|---|
| CN | 202740022 U | 2/2013 |
| CN | 104519960 B | 2/2018 |

(Continued)

OTHER PUBLICATIONS

Lee, Y. F., et al. "Nerve conduction block in diabetic rats using high-intensity focused ultrasound for analgesic applications." British journal of anaesthesia 114.5 (2015): 840-846. (Year: 2015).*
(Continued)

*Primary Examiner* — Sean D Mattson
(74) *Attorney, Agent, or Firm* — Fletcher Yoder, P.C.

(57)     ABSTRACT

Embodiments of the present disclosure relate to techniques for facilitating personalized neuromodulation treatment protocols. In one embodiment, a predetermined treatment position of an energy application device is used to guide future treatments for the patient. In one embodiment, a position of the energy application device relative to the predetermined treatment position is determined. In one embodiment, a total dose of ultrasound energy applied to the region of interest is determined.

20 Claims, 20 Drawing Sheets

Related U.S. Application Data continuation of application No. 16/121,223, filed on Sep. 4, 2018, now Pat. No. 11,235,178.

(52) U.S. Cl.
CPC ........... *A61B 8/4209* (2013.01); *A61B 8/4263* (2013.01); *A61N 2007/0026* (2013.01); *A61N 2007/0052* (2013.01)

(58) Field of Classification Search
CPC ... A61B 8/4245; A61B 8/4254; A61B 8/4209; A61B 8/4263; A61B 8/0891; A61B 8/488; A61B 8/085; A61B 8/546; A61B 8/4218; A61B 8/461; A61B 90/361; A61B 90/37; A61B 90/90; A61B 90/94; A61B 90/98; A61B 90/96; A61B 2017/00154; A61B 2034/2048; A61B 2034/2051; A61B 2034/2055; A61B 2090/3941; A61B 2090/0807; A61B 2090/378; A61B 2090/395; A61B 5/4848
See application file for complete search history.

(56) References Cited

U.S. PATENT DOCUMENTS

| | | | |
|---|---|---|---|
| 6,662,052 | B1 | 12/2003 | Sarwal et al. |
| 7,937,145 | B2 | 5/2011 | Dobak |
| 8,430,805 | B2 | 4/2013 | Burnett et al. |
| 9,248,286 | B2 | 2/2016 | Simon et al. |
| 11,235,178 | B2 | 2/2022 | Puleo et al. |
| 2002/0091339 | A1 | 7/2002 | Horzewski et al. |
| 2004/0019270 | A1* | 1/2004 | Takeuchi ................. A61B 8/14 |
| | | | 600/407 |
| 2008/0021321 | A1 | 1/2008 | Guracar et al. |
| 2009/0088623 | A1 | 4/2009 | Vortman et al. |
| 2010/0160781 | A1 | 6/2010 | Carter et al. |
| 2011/0009734 | A1* | 1/2011 | Foley ....................... A61N 7/02 |
| | | | 601/2 |
| 2011/0092781 | A1 | 4/2011 | Gertner |
| 2012/0157842 | A1 | 6/2012 | Davis et al. |
| 2013/0144165 | A1* | 6/2013 | Ebbini ................ G01S 7/52046 |
| | | | 600/439 |
| 2013/0178910 | A1* | 7/2013 | Azamian .............. A61K 9/0019 |
| | | | 607/33 |
| 2013/0296743 | A1 | 11/2013 | Lee et al. |
| 2014/0213903 | A1* | 7/2014 | Seo ....................... A61B 8/5207 |
| | | | 601/3 |
| 2015/0151142 | A1 | 6/2015 | Tyler et al. |
| 2016/0059044 | A1 | 3/2016 | Gertner |
| 2016/0106381 | A1* | 4/2016 | Aase .................. A61B 17/3403 |
| | | | 600/459 |
| 2016/0121142 | A1* | 5/2016 | Zhang .................. A61B 8/4254 |
| | | | 601/2 |
| 2016/0135762 | A1 | 5/2016 | Mihailescu et al. |
| 2016/0296769 | A1* | 10/2016 | Barthe ...................... A61N 7/00 |
| 2017/0027645 | A1 | 2/2017 | Oren et al. |
| 2017/0086785 | A1* | 3/2017 | Bjaerum .............. A61B 8/4444 |
| 2017/0105701 | A1 | 4/2017 | Pelissier et al. |
| 2017/0181726 | A1* | 6/2017 | Schneider .............. A61B 8/585 |
| 2017/0209694 | A1 | 7/2017 | Thompson et al. |
| 2017/0246482 | A1 | 8/2017 | Hananel et al. |
| 2017/0273665 | A1 | 9/2017 | Kapoor et al. |
| 2018/0028841 | A1 | 2/2018 | Konofagou et al. |
| 2018/0207450 | A1* | 7/2018 | Sanchez .................. A61N 7/00 |

FOREIGN PATENT DOCUMENTS

| | | |
|---|---|---|
| JP | 2013223728 A | 10/2013 |
| JP | 2015165894 A | 9/2015 |
| WO | 2014013285 A1 | 1/2014 |
| WO | 2018081826 A1 | 5/2018 |

OTHER PUBLICATIONS

Ativanichayaphong et al., "A combined wireless neural stimulating and recording system for study of pain processing," Journal of Neuroscience Methods, vol. 170, Issue: 1, pp. 25-34, May 15, 2008.
PCT/US2019/048901; International Search Report/Written Opinion mailed Dec. 4, 2019; 16 pages.
JP application 2021-511595 filed Feb. 27, 2021—Office Action issued Jun. 14, 2023; Machine Translation; 12 pages.
JP2013-223728 English Abstract; Espacenet search result sep. 13, 2023; 1 page.
JP2015-165894 English Abstract; Espacenet search result Sep. 13, 2023.

* cited by examiner

92

94

96

Patient w/probe

Probe
tilted back to
IMU target

104

Steering controller (a)

(b)

104

Steering controller

NEUROMODULATION ENERGY APPLICATION TECHNIQUES

CROSS-REFERENCE TO RELATED APPLICATIONS

The present application is a continuation U.S. patent application Ser. No. 17/572,383, filed on Jan. 10, 2022, now U.S. Pat. No. 11,911,634, which is a continuation of U.S. patent application Ser. No. 16/121,223, filed on Sep. 4, 2018, now U.S. Pat. No. 11,235,178, the disclosures of which are incorporated by reference in their entireties.

BACKGROUND

The subject matter disclosed herein relates to techniques to identify, target and/or dose regions of interest in a subject via application of neuromodulating energy to cause targeted physiological outcomes. In particular, the disclosed techniques may be part of a personalized or at-home neuromodulation treatment protocol.

Neuromodulation has been used to treat a variety of clinical conditions. For example, electrical stimulation at various locations along the spinal cord has been used to treat chronic back pain. An implantable device may periodically generate electrical energy that is applied to a tissue to activate certain nerve fibers, which may result in a decreased sensation of pain. With regard to spinal cord stimulation, the stimulating electrodes are generally positioned in the epidural space, although the pulse generator may be positioned somewhat remotely from the electrodes, e.g., in the abdominal or gluteal region, but connected to the electrodes via conducting wires. In other implementations, deep brain stimulation may be used to stimulate particular areas of the brain to treat movement disorders, and the stimulation locations may be guided by neuroimaging. Such central nervous system stimulation is generally targeted to the local nerve or brain cell function and is mediated by electrodes that deliver electrical pulses and that are positioned at or near the target nerves. However, positioning electrodes at or near the target nerves is challenging. For example, such techniques may involve surgical placement of the electrodes that deliver the energy. In addition, specific tissue targeting via neuromodulation is challenging. Electrodes that are positioned at or near certain target nerves mediate neuromodulation by triggering an action potential in the nerve fibers, which in turn results in neurotransmitter release at a nerve synapse and synaptic communication with the next nerve. Such propagation may result in a relatively larger or more diffuse physiological effect than desired, as current implementation of implanted electrodes stimulate many nerves or axons at once. Because the neural pathways are complex and interconnected, a more selective and targeted modulated effect may be more clinically useful.

BRIEF DESCRIPTION

Certain embodiments commensurate in scope with the claimed subject matter are summarized below. These embodiments are not intended to limit the scope of the claimed subject matter, but rather these embodiments are intended only to provide a brief summary of possible embodiments. Indeed, the disclosure may encompass a variety of forms that may be similar to or different from the embodiments set forth below.

In one embodiment, a neuromodulation system is provided that includes an ultrasound probe comprising an ultrasound transducer configured to apply ultrasound energy to a region of interest in a patient's body in an amount effective to induce neuromodulation of one or more nerve pathways. The system also includes a controller configured to control application of the ultrasound energy to the region of interest via the ultrasound probe; receive position information related to a position of the ultrasound probe; determine a position of the ultrasound probe relative to a predetermined treatment position; and determine a total dose of ultrasound energy applied to the region of interest.

In another embodiment, a neuromodulation system is provided. The system includes an ultrasound probe configured to apply energy to a region of interest in a patient's body, the ultrasound probe comprising an ultrasound therapy transducer and at least one position feedback device comprising a position sensor, a position fixture, a camera, an ultrasound imaging transducer, or a combination thereof, the position feedback device configured to generate information related to a position of the ultrasound probe; and a controller configured to: control application of the energy to the region of interest via the ultrasound probe; receive the information related to the position of the ultrasound probe; determine the position of the ultrasound probe relative to a predetermined treatment position based on the information; and determine a total dose of energy applied to the region of interest.

In another embodiment, a method is provided that includes the steps of positioning an ultrasound transducer to deliver ultrasound energy to a region of interest in a patient's body; determining that the position of the ultrasound transducer aligns with a predetermined treatment position; initiating application of energy from the ultrasound transducer to deliver to the region of interest a dose of energy in an amount effective to induce neuromodulation of one or more nerve pathways after determining that the position aligns with the predetermined treatment position; determining a total dose applied to the region of interest; and discontinuing the application of energy from the ultrasound transducer when the total dose is greater than or equal to a predetermined threshold.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
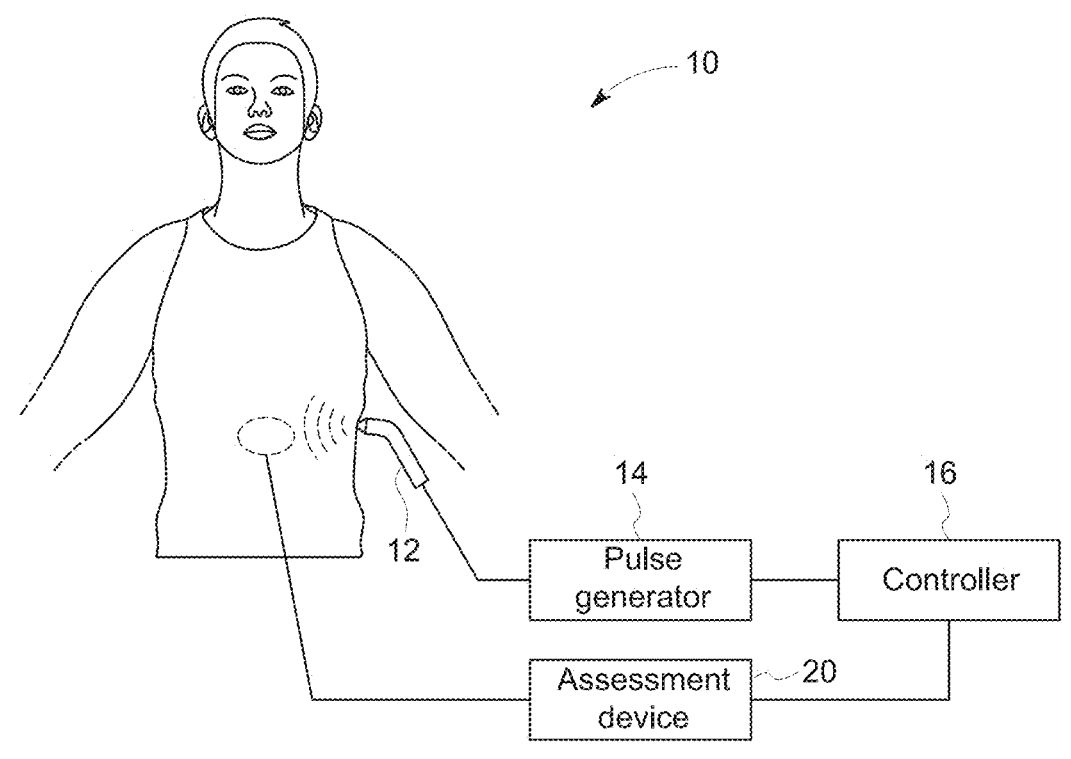
FIG. 1 is a schematic representation of a neuromodulation system using a pulse generator according to embodiments of the disclosure.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Any examples or illustrations given herein are not to be regarded in any way as restrictions on, limits to, or express definitions of, any term or terms with which they are utilized. Instead, these examples or illustrations are to be regarded as being described with respect to various particular embodiments and as illustrative only. Those of ordinary skill in the art will appreciate that any term or terms with which these examples or illustrations are utilized will encompass other embodiments that may or may not be given therewith or elsewhere in the specification and all such embodiments are intended to be included within the scope of that term or terms. Language designating such non-limiting examples and illustrations includes, but is not limited to: "for example," "for instance," "such as," "e.g.," "including," "in certain embodiments", "in some embodiments", and "in one (an) embodiment."

Provided herein are techniques for neuromodulation of targeted regions of interest as part of a treatment protocol that permits reproducible and reliable application of energy to a particular region or regions of interest over the course of the treatment protocol. The disclosed techniques may, in certain embodiments, be used in conjunction with personalized neuromodulation treatment protocols. For certain patients, a treatment protocol may include energy application, e.g., noninvasive ultrasound or mechanical energy application, to a region of interest of the patient at intervals according to the patient's particular clinical needs and at doses associated with targeted physiological outcomes. Depending on the length of the interval (e.g., intervals of hours, days, or weeks) between energy applications, it may be inconvenient and cumbersome to have the patient receive neuromodulating energy in a doctor's office at each treatment time. Accordingly, it would be beneficial to permit the patient to receive the neuromodulating energy according to the treatment protocol at home, either via self-directed delivery or with the help of a family member or caregiver. However, because patients do not typically have skills or training in medical device operation, it may be challenging to train a patient to manage their own neuromodulation treatment. Further, each patient's treatment protocol may be personalized and vary from patient-to-patient according to variations in anatomy, clinical condition of the patient, and responsiveness of the patient to energy to generate the targeted physiological outcome. For example, a treatment protocol for treating a particular disorder may target a particular region of interest (e.g., a region of a liver, pancreas, or other tissue). An effective energy application site associated with neuromodulating energy targeting the region of interest may be at one site for one patient and a slightly different site for another patient due to differences in patient anatomy.

The neuromodulation techniques disclosed herein facilitate validating a predetermined treatment position for an energy application device, whereby a predetermined treatment position is a location on the patient's body that, when the energy application device is positioned at the predetermined treatment position as provided herein, the energy applied affects a desired region of interest in the patient's body to achieve a targeted physiological outcome. Once established, the patient is able to administer neuromodulating energy to the region of interest when the energy application device is properly positioned at the predetermined treatment position. Further, the disclosed techniques provide feedback to the patient to indicate successful positioning of the energy application device at the predetermined treatment position and/or unsuccessful positioning of the energy application device outside of the predetermined treatment position. Such techniques may also be used in conjunction with multi-site or more complex neuromodulation protocols to guide patients to administer their own treatments. Further, the disclosed techniques provide quality checks for proper positioning to prevent inadvertent off-site energy application.

To that end, the disclosed neuromodulation techniques may be used in conjunction with a neuromodulation system configured to be used to administer neuromodulating energy as part of a treatment protocol. FIG. 1 is a schematic representation of a system 10 for neuromodulation to achieve neuromodulating effects such as neurotransmitter release and/or activation of components (e.g., the presynaptic cell, the postsynaptic cell) of a synapse in response to an application of energy. The depicted system includes a pulse generator 14 coupled to an energy application device 12 (e.g., an ultrasound transducer). The energy application device 12 is configured to receive energy pulses, e.g., via leads or wireless connection, that in use are directed to a region of interest of an internal tissue or an organ of a subject, which in turn results in a targeted physiological outcome.

In certain embodiments, the energy application device 12 and/or the pulse generator 14 may communicate wirelessly, for example with a controller 16 that may in turn provide instructions to the pulse generator 14. In other embodiments, the pulse generator 14 may be an extracorporeal device, e.g., may operate to apply energy transdermally or in a noninvasive manner from a position outside of a subject's body, and may, in certain embodiments, be integrated within the controller 16. In embodiments in which the pulse generator 14 is extracorporeal, the energy application device 12 may be operated by a caregiver and positioned at a spot on or above a subject's skin such that the energy pulses are delivered transdermally to a desired internal tissue. Once positioned to apply energy pulses to the desired site, the system 10 may initiate neuromodulation of one or more nerve pathways to achieve targeted physiological outcome or clinical effects. In other embodiments, the pulse generator 14 and/or the energy application device 12 may be implanted at a biocompatible site (e.g., the abdomen) and may be coupled the energy application device 12 and the pulse generator 14 internally, e.g., via one or more leads.

In certain embodiments, the system 10 may include an assessment device 20 that is coupled to the controller 16 and that assesses characteristics that are indicative of whether the targeted physiological outcome of the modulation have been achieved. In one embodiment, the targeted physiological outcome may be local. For example, the modulation of one or more nerve pathways may result in local tissue or function changes, such as tissue structure changes, local change of concentration of certain molecules, tissue displacement, increased fluid movement, etc. The targeted physiological outcome may be a goal of the treatment protocol.

The modulation of one or more nerve pathways to achieve a targeted physiological outcome may result in systemic or non-local changes, and the targeted physiological outcome may be related to a change in concentration of circulating molecules or a change in a characteristic of a tissue that does not include the region of interest to which energy was directly applied. In one example, the displacement may be a proxy measurement for a desired modulation, and displacement measurements below an expected displacement value may result in modification of modulation parameters until an expected displacement value is induced. Accordingly, the assessment device 20 may be configured to assess concentration changes in some embodiments. In some embodiments, the assessment device 20 may be an imaging device configured to assess changes in organ size position, and/or tissue characteristics. In another embodiment, the assessment device 20 may be a circulating glucose monitor. While the depicted elements of the system 10 are shown separately, it should be understood that some or all of the elements may be combined with one another. In another embodiment, the assessment device may assess local temperature rises of the tissue, which may be detected using a separate temperature sensor or ultrasound imaging data from the energy application device 12 when configured for ultrasound energy application. Assessment of speed of sound differences may be detected through difference imaging techniques pre/during/post therapy.

Further, some or all of the elements may communicate in a wired or wireless manner with one another.

Based on the assessment, the modulation parameters of the controller 16 may be altered such that an effective amount of energy is applied. For example, if a desired modulation is associated with a change in concentration (circulating concentration or tissue concentration of one or more molecules) within a defined time window (e.g., 5 minutes, 30 minutes after a procedure of energy application starts) or relative to a baseline at the start of a procedure, a change of the modulation parameters such as pulse frequency or other parameters may be desired, which in turn may be provided to the controller 16, either by an operator or via an automatic feedback loop, for defining or adjusting the energy application parameters or modulation parameters of the pulse generator 14 until the modulation parameters result in an effective amount of energy being applied.

The system 10 as provided herein may provide energy pulses according to various modulation parameters as part of a treatment protocol to apply the effective amount of energy. For example, the modulation parameters may include various stimulation time patterns, ranging from continuous to intermittent. With intermittent stimulation, energy is delivered for a period of time at a certain frequency during a signal-on time. The signal-on time is followed by a period of time with no energy delivery, referred to as signal-off time. The modulation parameters may also include frequency and duration of a stimulation application. The application frequency may be continuous or delivered at various time periods, for example, within a day or week. Further, the treatment protocol may specify a time of day to apply energy or a time relative to eating or other activity. The treatment duration to cause the targeted physiological outcomes may last for various time periods, including, but not limited to, from a few minutes to several hours. In certain embodiments, treatment duration with a specified stimulation pattern may last for one hour, repeated at, e.g., 72 hour intervals. In certain embodiments, energy may be delivered at a higher frequency, say every three hours, for shorter durations, for example, 30 minutes. The application of energy, in accordance with modulation parameters, such as the treatment duration, frequency, and amplitude, may be adjustably controlled to achieve a desired result.

Figure 2:
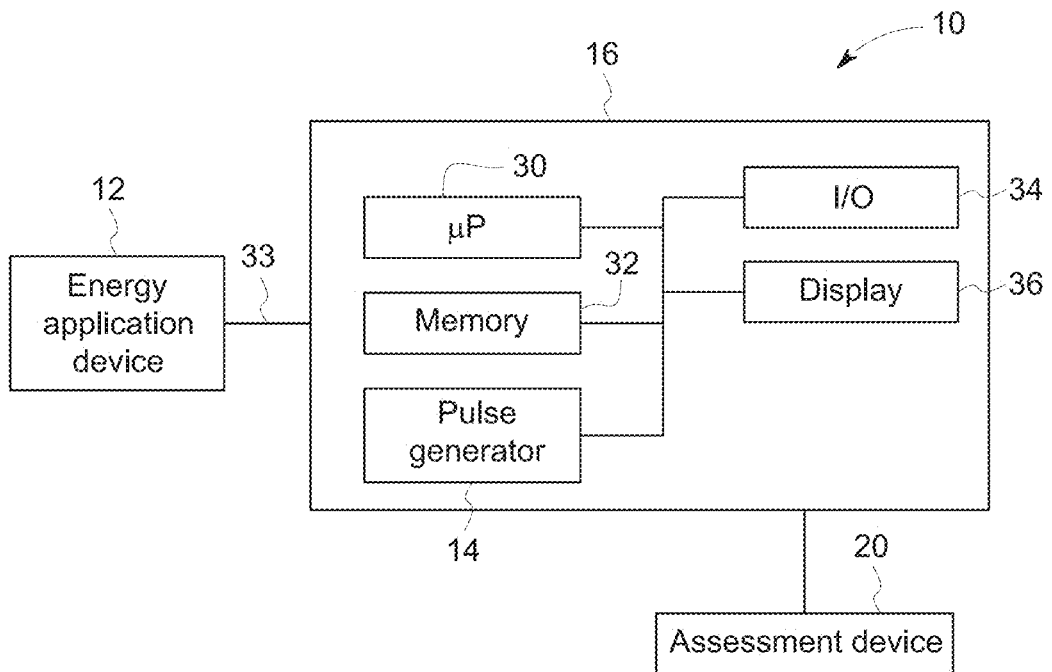
FIG. 2 is a block diagram of a neuromodulation system according to embodiments of the disclosure.

FIG. 2 is a block diagram of certain components of the system 10. As provided herein, the system 10 for neuromodulation may include a pulse generator 14 that is adapted to generate a plurality of energy pulses for application to a tissue of a subject. The pulse generator 14 may be separate or may be integrated into an external device, such as a controller 16. The controller 16 includes a processor 30 for controlling the device. Software code or instructions are stored in memory 32 of the controller 16 for execution by the processor 30 to control the various components of the device. The controller 16 and/or the pulse generator 14 may be connected to the energy application device 12 via one or more leads 33 or wirelessly.

The controller 16 also includes a user interface with input/output circuitry 34 and a display 36 that are adapted to allow a clinician to provide selection inputs or modulation parameters to modulation programs. Each modulation program may include one or more sets of modulation parameters including pulse amplitude, pulse width, pulse frequency, etc. The pulse generator 14 modifies its internal parameters in response to the control signals from controller device 16 to vary the stimulation characteristics of energy pulses transmitted through lead 33 to an subject to which the energy application device 12 is applied. Any suitable type of pulse generating circuitry may be employed, including but not limited to, constant current, constant voltage, multiple-independent current or voltage sources, etc. The energy applied is a function of the current amplitude and pulse width duration. The controller 16 permits adjustably controlling the energy by changing the modulation parameters and/or initiating energy application at certain times or cancelling/suppressing energy application at certain times. In one embodiment, the adjustable control of the energy application device to apply the effective amount of energy is based on information about a concentration of one or more molecules in the subject (e.g., a circulating molecule). If the information is from the assessment device 20, a feedback loop may drive the adjustable control. For example, a diagnosis may be made based on circulating glucose concentration, as measured by the assessment device 20, in response to neuromodulation. When the concentration is above a predetermined threshold or range, the controller 16 may initiate a treatment protocol of energy application to a region of interest (e.g., liver) and with modulation parameters that are associated with a reduction in circulating glucose. The treatment protocol may use different modulation parameters than those used in the diagnosis protocol (e.g., higher energy levels, more frequent application).

In one embodiment, the memory 32 stores different operating modes that are selectable by the operator. For example, the stored operating modes may include instructions for executing a set of modulation parameters associated with a particular treatment site, such as regions of interest in the liver, pancreas, gastrointestinal tract, spleen. Different sites may have different associated modulation parameters. Rather than having the operator manually input the modes, the controller 16 may be configured to execute the appropriate instruction based on the selection. In another embodiment, the memory 32 stores operating modes for different types of procedures. For example, activation may be associated with a different stimulating pressure or frequency range relative to those associated with depressing or blocking tissue function.

In a specific example, when the energy application device is an ultrasound transducer, the effective amount of energy may involve predetermined temporal average intensity applied to a region of interest. For example, the effective amount of energy may include a time-averaged power (temporal average intensity) and peak positive pressure in the range of 1 mW/cm2-30,000 mW/cm2 (temporal average intensity) and 0.1 MPa to 7 MPa (peak pressure). In one example, the temporal average intensity is less than 35 W/cm2 in the region of interest to avoid levels associated with thermal damage & ablation/cavitation. In another specific example, when the energy application device is a mechanical actuator, the amplitude of vibration is in the range of 0.1 to 10 mm. The selected frequencies may depend on the mode of energy application, e.g., ultrasound or mechanical actuator. The controller 16 may be capable of operating in a validating mode to acquire a predetermined treatment position and the predetermined treatment position may be implemented as part of a treatment operating mode that is configured to execute a treatment protocol when the energy application device 12 is positioned at the predetermined treatment position.

The system may also include an imaging device that facilitates focusing the energy application device 12. In one embodiment, the imaging device may be integrated with or the same device as the energy application device 12 such that different ultrasound parameters (frequency, aperture, or energy) are applied for selecting (e.g., spatially selecting) a region of interest and for focusing energy to the selected region of interest for targeting and subsequently neuromodulation. In another embodiment, the memory 32 stores one or more targeting or focusing modes that is used to spatially select the region of interest within an organ or tissue structure. Spatial selection may include selecting a subregion of an organ to identify a volume of the organ that corresponds to a region of interest. Spatial selection may rely on image data as provided herein. Based on the spatial selection, the energy application device 12 may be focused on the selected volume corresponding to the region of interest. For example, the energy application device 12 may be configured to first operate in the validating mode to acquire the predetermined treatment position by capturing image data to be used for identifying the predetermined treatment position associated with capturing the region of interest. The validating mode energy is not at levels and/or applied with modulation parameters suitable for neuromodulating treatment. However, once the region of interest is identified, the controller 16 may then operate in a treatment mode according to the modulation parameters associated with achieving targeted physiological outcomes.

The controller 16 may also be configured to receive inputs related to the targeted physiological outcomes as an input to the selection of the modulation parameters. For example, when an imaging modality is used to assess a tissue characteristic, the controller 16 may be configured to receive a calculated index or parameter of the characteristic. Based on whether the index or parameter is above or below a predefined threshold, a diagnosis may be made, and an indication of the diagnosis may be provided (e.g., via a display). In one embodiment, the parameter can be a measure of tissue displacement of the affected tissue or a measure of depth of the affected tissue. Other parameters may include assessing a concentration of one or more molecules of interest (e.g., assessing one or more of a change in concentration relative to a threshold or a baseline/control, a rate of change, determining whether concentration is within a desired range). Further, the energy application device 12 (e.g., an ultrasound transducer) may operate under control of the controller 16 to a) acquire image data of a tissue that may be used to spatially select a region of interest within the target tissue b) apply the modulating energy to the region of interest and c) acquire image to determine that the targeted physiological outcome has occurred (e.g., via displacement measurement). In such an embodiment, the imaging device, the assessment device 20 and the energy application device 12 may be the same device.

Figure 3:
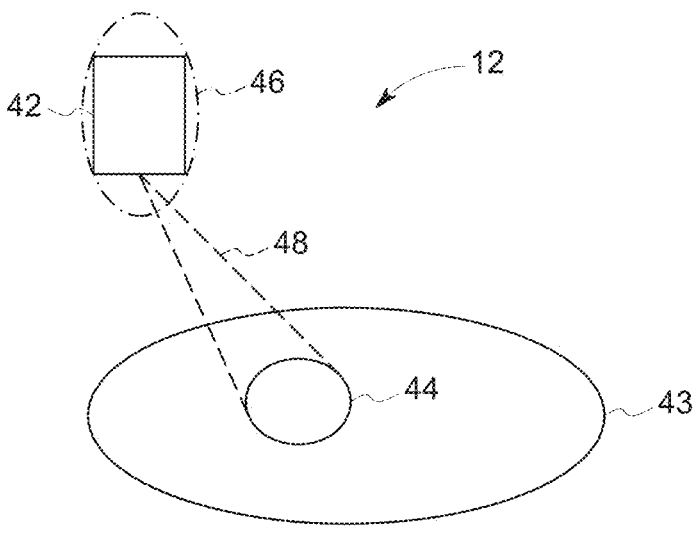
FIG. 3 is a schematic representation of a neuromodulation.

FIG. 3 is a specific example in which the energy application device 12 includes an ultrasound transducer 42 (e.g., a transducer array) that is capable of applying energy to a target tissue 43, e.g., a liver, a spleen, a pancreas. The energy application device 12 may include control circuitry for controlling the ultrasound transducer 42. The control circuitry of the processor 30 (FIG. 2) may be integral to the energy application device 12 (e.g., via an integrated controller 16) or may be a separate component. The ultrasound transducer 42 may also be configured to acquire image data to assist with spatially selecting a desired or targeted region of interest 44 and focusing the applied energy on the region of interest of the target tissue or structure.

The desired target tissue 43 may be an internal tissue or an organ that includes synapses of axon terminals and non-neuronal cells. The synapses may be stimulated by direct application of energy to the axon terminals within a field of focus or focal zone 48 of the ultrasound transducer 42 focused on a region of interest 44 of the target tissue 43 to cause release of molecules into the synaptic space, e.g., the release of neurotransmitters and/or the change in ion channel activity in turn causes downstream effects. The region of interest 44 may be selected to include a certain type of axon terminal, such as an axon terminal of a particular neuron type and/or one that forms a synapse with a certain type of non-neuronal cell. Accordingly, the region of interest 44 may be selected to correspond to a portion of the target tissue 43 with the desired axon terminals (and associated non-neuronal cells). The energy application may be selected to preferentially trigger a release of one or more molecules such as neurotransmitters from the nerve within the synapse or directly activate the non-neuronal cell itself through direct energy transduction (i.e. mechanotransduction or voltage-activated proteins within the non-neuronal cells), or cause an activation within both the neural and non-neuronal cells that elicits a desired physiological effect. The region of interest 44 may be selected as the site of nerve entry into the organ. In one embodiment, liver stimulation or modulation may refer to a modulation of the region of interest 44 at or adjacent to the porta hepatis. Acquisition of the predetermined treatment position 46 may include selection of the region of interest 44, whereby the position on the patient's body at which the region of interest 44 is within the focal zone 48 of the energy application device 12 when in operation is the predetermined treatment position 46.

The energy may be focused or substantially concentrated on a region of interest 44 and to only part of the internal tissue 43, e.g., less than about 50%, 25%, 10%, or 5% of the total volume of the tissue 43. That is, the region of interest 44 may be a sub-region of the internal tissue 43. In one embodiment, energy may be applied to two or more regions of interest 44 in the target tissue 43, and the total volume of the two or more regions of interest 44 may be less than about 90%, 50%, 25%, 10%, or 5% of the total volume of the tissue 43. In one embodiment, the energy is applied to only about 1%-50% of the total volume of the tissue 43, to only about 1%-25% of the total volume of the tissue 43, to only about 1%-10% of the total volume of the tissue 43, or to only about 1%-5% of the total volume of the tissue 43. In certain embodiments, only axon terminal in the region of interest 44 of the target tissue 43 would directly receive the applied energy and release neurotransmitters while the unstimulated axon terminals outside of the region of interest 44 do not receive substantial energy and, therefore, are not activated/stimulated in the same manner. In some embodiments, axon terminals in the portions of the tissue directly receiving the energy would induce an altered neurotransmitter release. In this manner, tissue subregions may be targeted for neuromodulation in a granular manner, e.g., one or more subregions may be selected. In some embodiments, the energy application parameters may be chosen to induce preferential activation of either neural or non-neuronal components within the tissue directly receiving energy to induce a desired combined physiological effect. In certain embodiments, the energy may be focused or concentrated within a volume of less than about 25 mm³. In certain embodiments, the energy may be focused or concentrated within a volume of about 0.5 mm³-50 mm³. A focal volume and a focal depth for focusing or concentrating the energy within the region of interest 44 may be influenced by the size/configuration of the energy application device 12. The focal volume of the energy application may be defined by the field of focus or focal zone of the energy application device 12.

As provided herein, the energy may be substantially applied only to the region or regions of interest 44 to preferentially activate the synapse in a targeted manner to achieve targeted physiological outcomes. Accordingly, in certain embodiments, only a subset of a plurality of different types of axon terminals in the tissue 43 is exposed to the direct energy application.

Figure 4:
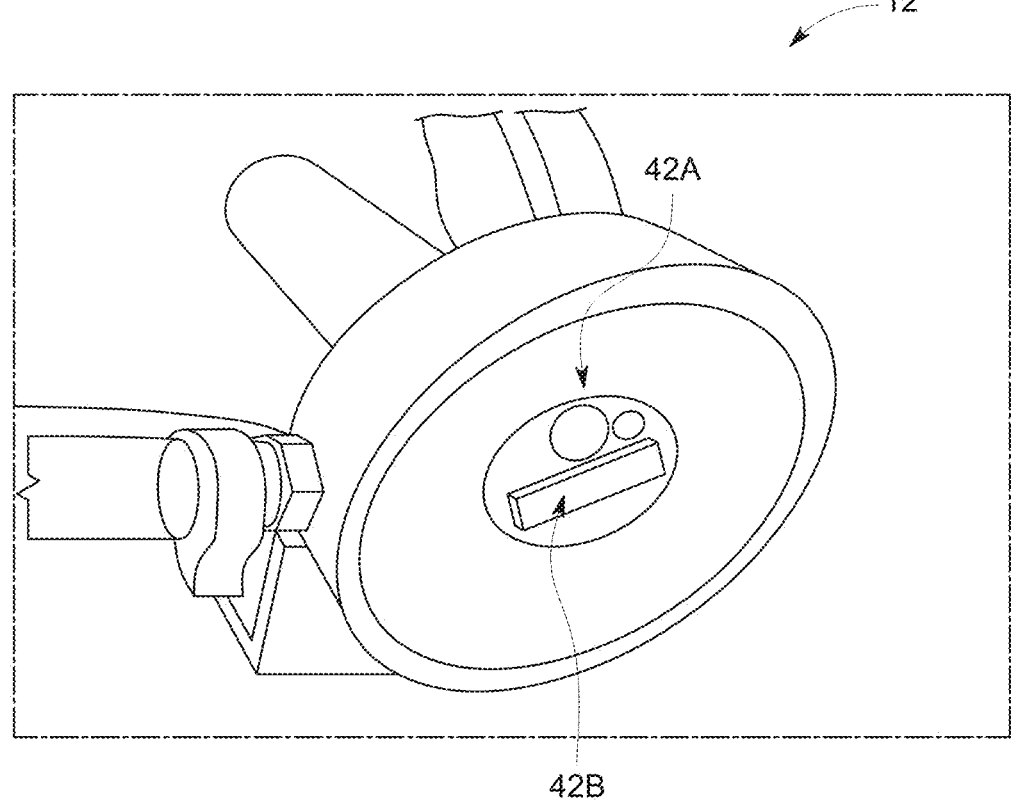
FIG. 4 is a schematic representation of an ultrasound energy application device in operation according to embodiments of the disclosure.

The energy application device 12 may be configured as an extracorporeal non-invasive device or an internal device, e.g., a minimally invasive device. As noted, the energy application device 12 may be an extracorporeal noninvasive ultrasound transducer or mechanical actuator. For example, FIG. 4 shows an embodiment of the energy application device 12 configured as a handheld ultrasound probe including an ultrasound transducer 42. However, it should be understood that other noninvasive implementations are also contemplated, including other methods to configure, adhere, or place ultrasound transducer probes over an anatomical target. Further, in addition to handheld configurations, the energy application device 12 may include steering mechanisms responsive to instructions from the controller 16. The steering mechanisms may orient or direct the energy application device 12 towards the target tissue 43 (or structure), and the controller 16 may then focus the energy application onto the region of interest 44. The ultrasound transducer 42 may include an imaging transducer 42A used for spatial selection of the region of interest 44 within the target tissue 43. The ultrasound transducer 42 may include a treatment transducer 42B that applies the neuromodulation energy. In one embodiment, the energy application device 12 may include a MEMS transducer, such as a capacitive micromachined ultrasound transducer.

Figure 5:
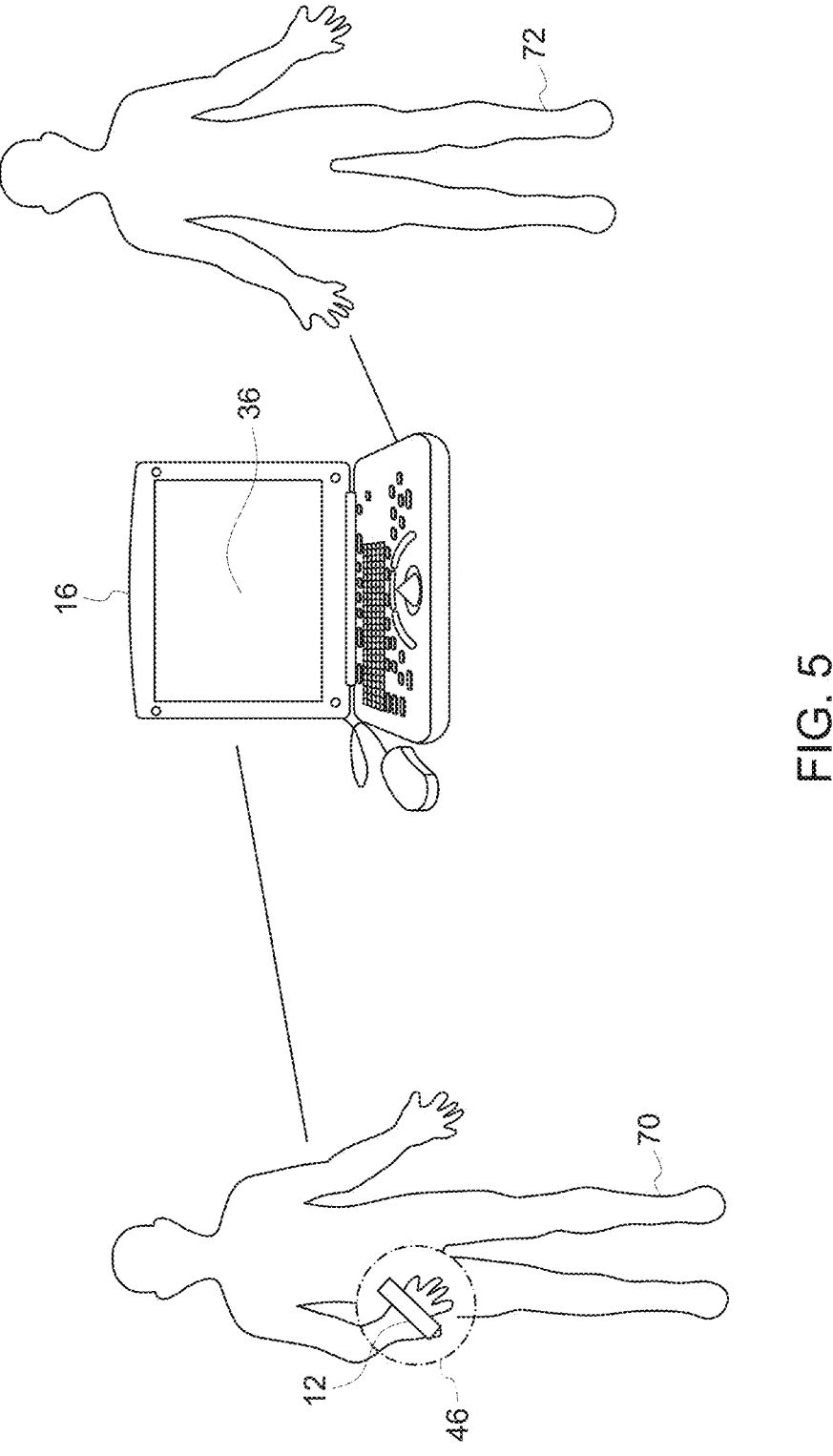
FIG. 5 is a schematic representation of a technique for establishing a predetermined treatment position according to embodiments of the disclosure.
Figure 6:
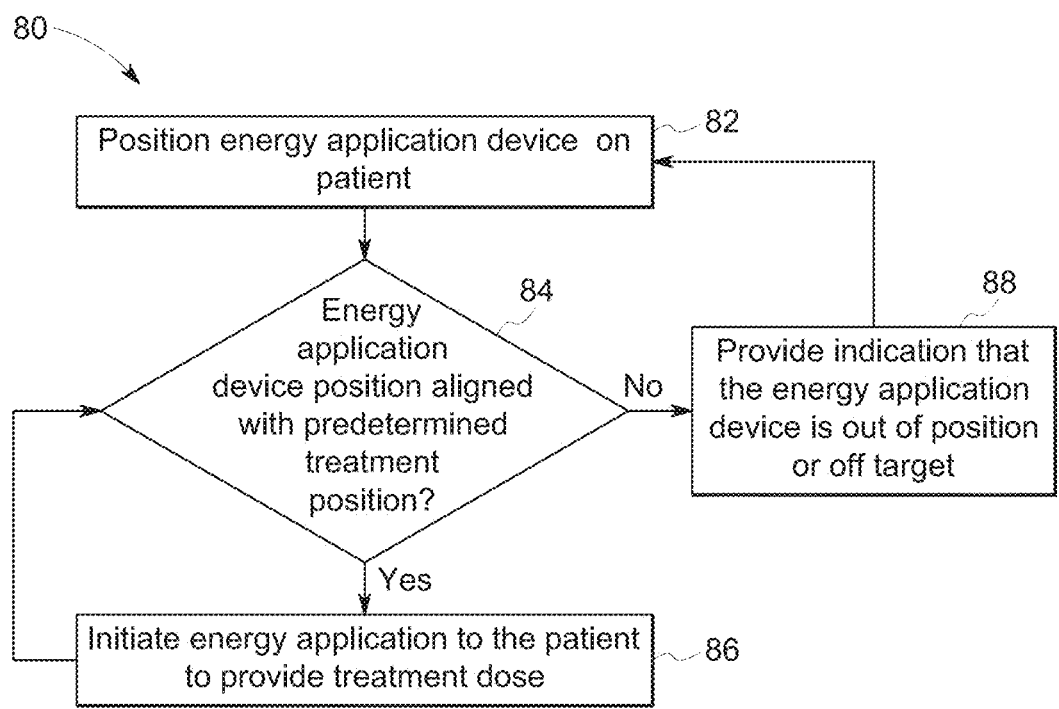
FIG. 6 is an embodiment of an image associated with a predetermined treatment position according to embodiments of the disclosure.

FIG. 5 is a schematic representation of a predetermined treatment position acquisition technique. The patient 70 may initiate a treatment protocol with an initial physician or skilled device operator 72 (e.g., ultrasound technician) meeting. The operator 72 acquires images from the device 12 positioned at one or more calibrating positions on the patient 70 (e.g., with the energy application device 12 in direct contact with the patient's skin). Using the images on the display 36 to guide positioning, the operator 72 instructs the patient 70 to move the device 12 until an image that includes the region of interest 44 is acquired. For example, as shown in FIG. 6, such an image may be a liver image that includes a porta hepatis region of interest. Fine positioning may further resolve the region of interest 44. The selection of the region of interest 44 and/or the predetermined treatment position 86, may include automatic selection via image segmentation algorithms that use acquired images to identify organs. The region of interest 44 may be selected to correspond to a certain % of target organ tissue within a target location/image. In another embodiment, Doppler information (i.e. certain level of blood flow in a specific location; like the porta hepatis in liver) or mechanical information (i.e. ultrasound reflectance or elastography data) may be used to select the region of interest 44.

It should be understood that the position as provided herein may include an angle, orientation, and/or pose of the energy application device 12. In one embodiment, the position may include an absolute position in space in three dimensions. Further, an energy application device 12 may be considered to be aligned when located at a correct area on the patient (e.g., on a particular area of the patient's skin, at a predetermined treatment position) and when the energy application device 12 is posed, angled, and/or oriented correctly relative to the patient in one or more degrees of freedom. The position information may also include an assessment of contact or pressure on the subject. This orientation may also be determined through use of external mechanical fixtures that either make contact with the patient, the patients clothing, or the chair/bed/support/area associated with the patient. In one example, a probe head or other portion of the energy application device fits on a mechanical fixture that is positioned on the predetermined treatment site of the patient through either a wearable or an external device (i.e. a therapy chair)). In one respect, the mechanical fixture is yet another example of a location of position sensor/controller.

In some embodiments, an ultrasound image may be used to guide the ultrasound stimulus to spatially select a region of interest for targeted delivery of ultrasound stimulus and, accordingly, identify the predetermined treatment position of the energy application device 12 on the patient that results in energy application to the region of interest. As provided herein, selecting the region of interest may include obtaining an image of a tissue or organ (or a portion of a tissue or organ) and, based on image (e.g., the ultrasound image), identifying a region of interest within the organ. In some embodiments, the tissue or organ may have anatomical features that are used to guide the selection of the region of interest within the organ. Such features may, in some embodiments, include a site of blood vessel or nerve entry into an organ, a tissue type within an organ, an interior or edge of an organ, or a suborgan structure, by way of non-limiting example. In certain embodiments, the anatomical feature may include a liver porta hepatis, suborgans of a gastrointestinal tract (stomach, small intestines, large intestines), a pancreatic duct, or a splenic white pulp. By identifying the anatomical features in the image, the region of interest may be selected to overlap with or include the anatomical feature or be adjacent to the anatomical feature. In other embodiments, the anatomical feature may be excluded from the region of interest. For example, an intestinal tissue may be selected as a region of interest rather than a stomach tissue. The identification of the anatomical feature may be via morphological features that are visible in the image (e.g., visible in the ultrasound image) or by structure recognition features of the imaging modality used to obtain the image. As disclosed herein, the system 10 may be configured such that the energy application device 12 is configured to operate in an imaging mode to obtain the image and to subsequently operate in energy application mode after the image is obtained and the region of interest is spatially selected based on the image.

In other embodiments, the region of interest may be identified by the presence or absence of one or more biological markers. Such markers may be assessed by staining the organ or tissue and obtaining images indicative of the stain to identify regions of the organ or tissue that include the biological marker/s. In some embodiments, the biological marker information may be obtained by in vivo labelling technologies to obtain location data of the biological marker/s in the tissue or organ specific for the subject in real time. In other embodiments, the biological marker information may be obtained by in vitro staining technologies to obtain location data for one or more representative images that is then used to predict the locations of the biological marker/s within the subject's tissue or organ. In some embodiments, the region of interest is selected to correspond with portion of the tissue or organ that are rich in a particular biological marker or that lack a particular biological marker. For example, the one or more biological markers may include markers for neuronal structures (e.g., myelin sheath markers).

The region of interest in the organ or tissue may be spatially selected based on operator input. For example, an operator may designate the region of interest on the obtained image by directly manipulating the image (i.e., drawing or writing the region of interest on the image) or by providing image coordinate information that corresponds to the region of interest. In another embodiment, the region of interest may be automatically selected based on the image data to achieve spatial selection. In some embodiments, the spatial selection includes storing data related to the region of interest in a memory and accessing the data. Once spatially selected, the system 10 is configured to apply energy to the region of interest as provided herein according to the treatment protocol.

Alternatively, as part of the training session with the doctor or caregiver, an entire patient-specific dataset is annotated by an expert. The dataset contains images that are both on-target and off-target, and a patient-specific deep learning (DL) model would be trained to recognize on-target locations. When in the home and using the device to apply the therapy, the system would run the DL image classification model in real-time to find on-target locations, at which point the therapy beam is able to be activated (or is associated with an on-target dose).

Once the energy application device 12 is positioned such that its focal zone 48 includes the region of interest 44, the operator 72 stores the acquired image as being the image associated with the predetermined treatment position 46. The predetermined treatment position 46 refers to a position of the energy application device 46 in or on the patient such that its focal zone 48 includes the region of interest 44. The predetermined treatment position 46 may include a region of surface area on the patient's skin (or clothing item) on which the energy application device 12 is positioned.

In one embodiment, the predetermined treatment position 46 may be identified with a mark, temporary tattoo, an implantable or surface position sensor, a sticker, or other indicator. Further, the indicator may be shaped to include the contours of the portion of the energy application device 12 in direct contact with the patient's skin or clothing item to permit the energy application device 12 to be oriented correctly during subsequent treatments. In other embodiments, as provided herein, position information for the energy application device 12 may also be acquired as representative of the predetermined treatment position 46. Indicator placement may occur during a specific dataset collection session before sending the patient home with the device 12, where the clinician would place the indicator/ tattoo on the patient skin at or close to the predetermined treatment position. Then, when scanning to find the predetermined treatment position, the user would click a button to initiate storing the target probe position. Then, the relative position and orientation between the on-probe camera and on-skin marker would be stored into memory as a patient-specific or device-specific calibration. In one embodiment, in subsequent scans when the patient is at home, the device finds the same relative alignment between the on-probe camera and the on-skin marker prior to activating the therapy beam.

The indicator may be visible or visible only under certain conditions (e.g., light of a certain frequency). The energy application device 12 may be configured to provide illumi-nation of the particular frequency by which the indicator is rendered visible. Further, the indicator may be encoded with patient-specific information (e.g., alphanumeric code, QR code) that, when scanned by an optical reader (e.g., a camera or optical scanner, which may be integrated into the energy application device 12), facilitates access of patient-associ-ated identification information and/or modulation param-eters. The indicator itself may also have embedded patient-specific information (a unique patient identifier) or even dose control parameters (the prescription). The system, upon reading the encoded information, may initiate a validation to confirm that the programmed therapy is being applied the right patient. In one specific example, the indicator is a tattoo is a QR code with a unique patient identifier, though other patterns are possible. The information in the QR code is encrypted to prevent access to the raw data if scanned with a common QR code reader. In this manner, the indicator provides an additional validation step. Other patient valida-tion techniques are also contemplated, including ultrasound imaging validations (comparing stored ultrasound images of the patient to acquired images as a validation), or biometric validation (e.g., facial recognition, fingerprint). Validation may be a precursor to initiating treatment such that, without validation, no energy application via the energy application device 12 is permitted. In one embodiment, the indicator may be formed from acoustically varying materials in a grid similar to a QR code, but with the blacks and white portions of the QR code instead made of materials with very different acoustic properties that are resolvable via ultrasound imag-ing or from materials with purposeful air gaps to reduce ultrasound coupling in the pattern. Accordingly, the indica-tor may be visible during ultrasound images in the near field of the ultrasound image, or as shadowing over a portion of the image.

When the patient 70 or other caregiver initiates subse-quent neuromodulation treatments as part of the treatment protocol, the energy application device 12 (either the same energy application device 12 used to acquire the predeter-mined treatment position 46 or a different energy application device 12 configured to operate in a similar manner) is positioned on the patient and a determination is made if the position aligns with (is the same as or overlaps significantly with) the predetermined treatment position 46. In one embodiment, the determination involves positioning the energy application device 12 on an indicator on the patient. When positioned on the indicator, the energy application device 12 is considered to be in position.

Figure 7:
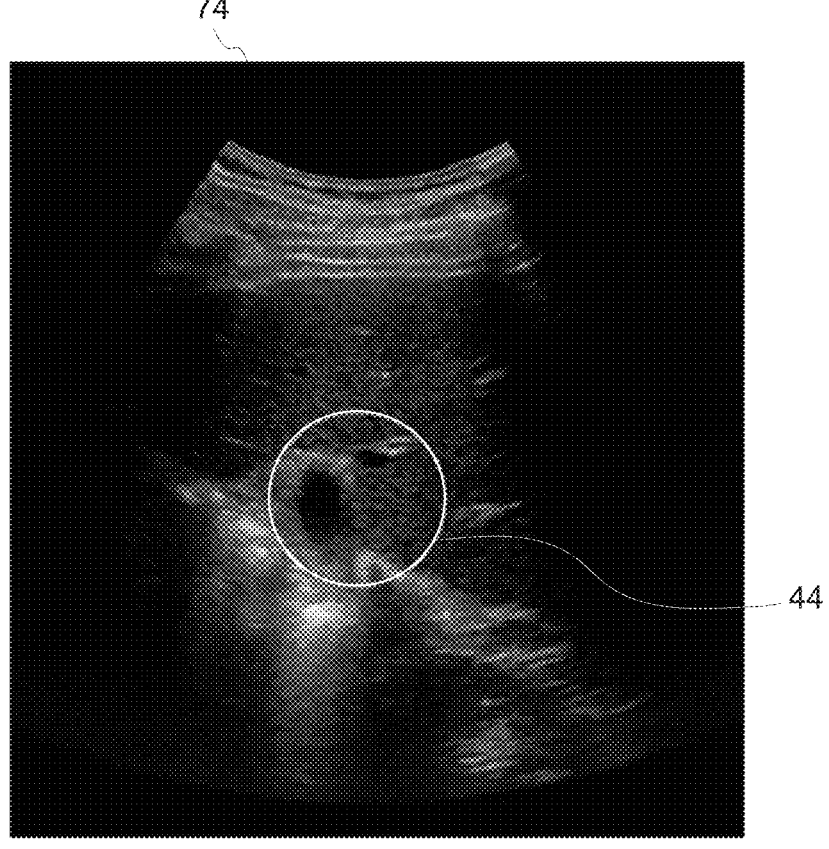
FIG. 7 is a flow diagram of a neuromodulation technique according to embodiments of the disclosure.

In other embodiments, the system 10 may be configured to automatically control energy application based on the position of the energy application device. FIG. 7 is a flow diagram of a method 80 for controlling energy application based on correspondence of the energy application device 12 to a predetermined treatment position 46. The patient may position the energy application device (block 82) at a general location of the predetermined treatment position 46, e.g., using a skin indicator or by memory. The system 10 may then acquire information about the position of the energy application device 12 and determine if the energy applica-tion device is aligned with the predetermined treatment position (block 84).

Figure 10:
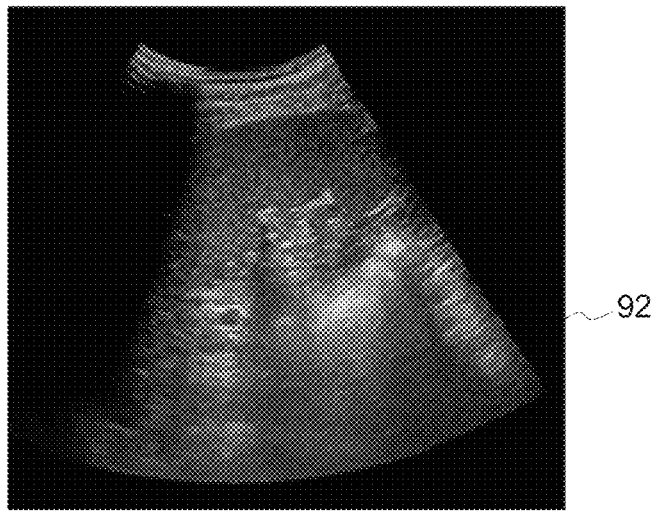
FIG. 10 shows an embodiment of a patient-mediated steering instruction based on position and/or image information according to embodiments of the disclosure
Figure 10:
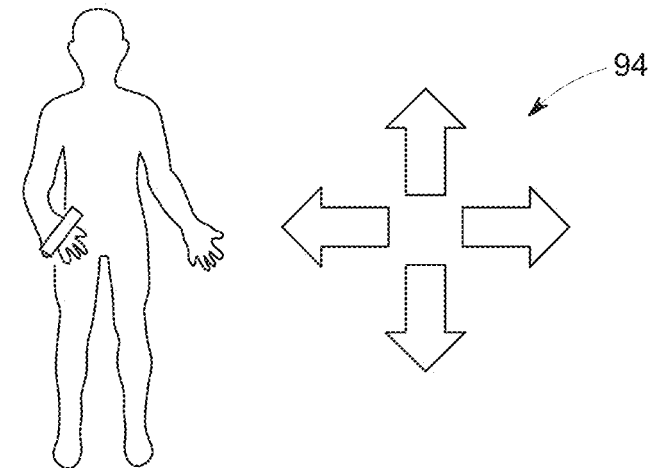
Figure 10:
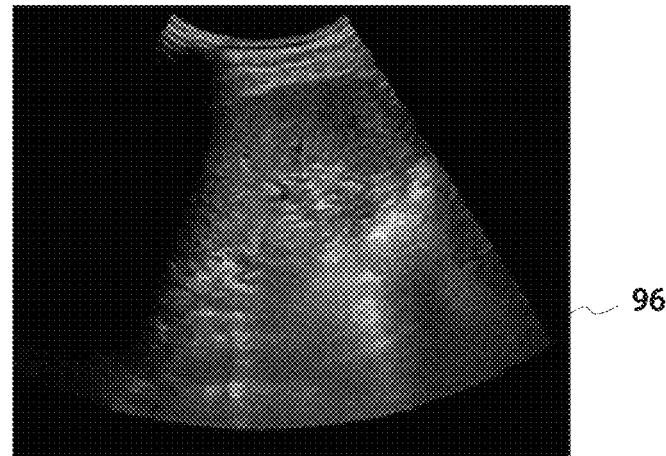

For example, the system 10 may acquire ultrasound images at various positions of the energy application device 12 (e.g., the patient 70 may move the energy application device in a limited area on the body near the predetermined treatment position 46. Once an image is acquired that aligns with an ultrasound image acquired from the energy appli-cation device 12 at the predetermined treatment position 46, the energy application device 12 is considered to be on target or in position. The image alignment may be performed using image registration techniques. In another embodiment, addi-tionally or alternatively, position information from one or more sensors (see FIG. 10) on the energy application device 12, the patient 70, or both may be used to determine if the position of the energy application device 12 aligns with the predetermined treatment position 46.

Figure 8:
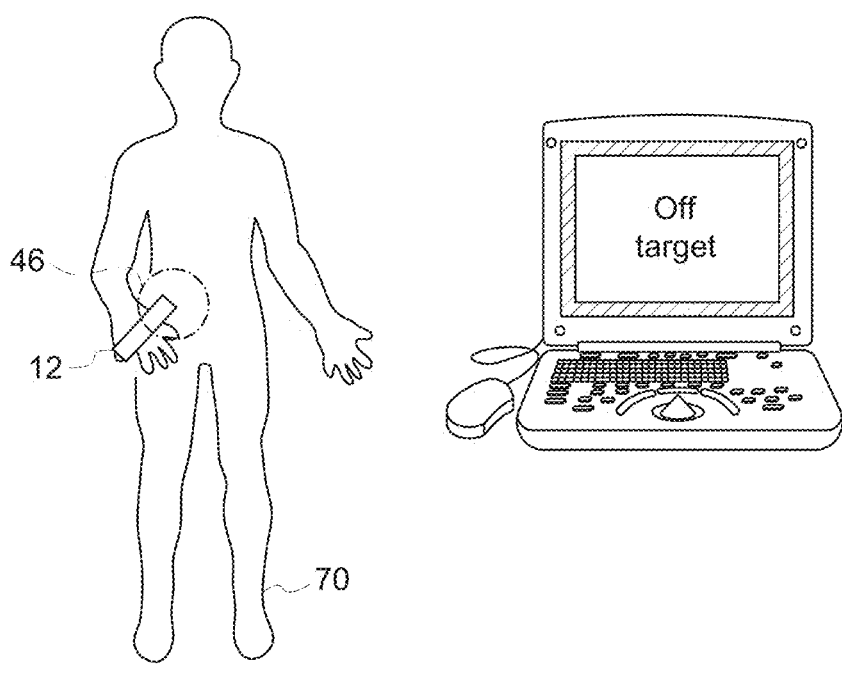
FIG. 8 is a schematic representation of an off-target position of an energy application device and an associated indication according to embodiments of the disclosure.
Figure 9:
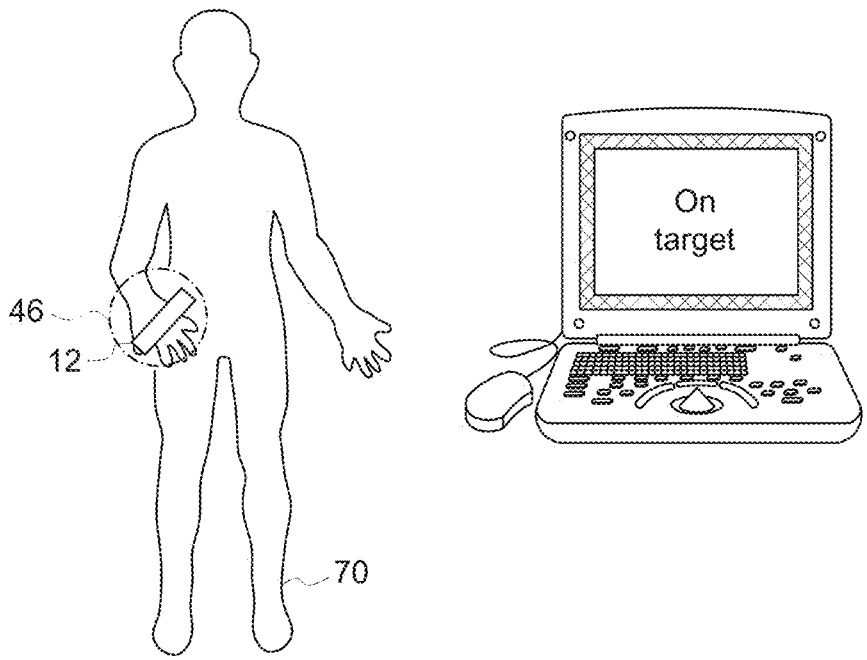
FIG. 9 is a schematic representation of an on-target position of an energy application device and an associated indication according to embodiments of the disclosure.

Based on the determination, treatment may be initiated when the energy application device is aligned with the predetermined treatment position 46 (block 86) and may be prohibited when the energy application device is not aligned with the predetermined treatment position 46. That is, the system 10 may be configured such that the pulse generator 16 is not permitted to drive the energy application device 12 when the energy application device 12 is not aligned with the predetermined treatment position 46. For example, the energy application may only be permitted to occur subse-quent to or during an alignment signal generation indicating alignment with the predetermined treatment position 46. If the position of the energy application device 12 does not align with the predetermined treatment position 46, an indication of misalignment may be provided (block 88). The method 80 may iterate to update control of the energy application based on any shifts or updates in movement of the energy application device 12 relative to the predeter-mined treatment position 46 on the patient FIG. 8 is a schematic representation of an indication provided in the case of an off-target energy application device 12, and FIG. 9 is a schematic representation of an indication provided in the case of an on-target energy application device 12. As shown, the off-target energy application device 12 is partially within but not entirely within a region associated with a predetermined treatment position 46 while the on-target energy application device 12 is entirely within a region associated with a predetermined treatment position 46. The system 10 may be configured to permit a certain level of tolerance or deviation from a predetermined treatment position 46 and still be considered on-target. In one embodiment, the energy application device 12 is considered to be off-target based on a degree of mismatch with the acquired image associated with the predetermined treatment position 46. For example, less than a 90% match per image registration may be indicative of an off-target position while a 90% or greater match may be on-target. In another embodiment, the energy application device 12 is considered to be off-target or on-target based on a position relative to an indicator, such as a mark or tattoo on the skin or worn item of the patient, or relative to a mechanical fixture located on the patient and/or on an external piece of equipment (e.g. chair) associated with the patient's position. The energy application device 12 may include one or more sensors that sense the indicator and provide feedback to the system 10 related to a position of the energy application device 12 relative to the indicator. The energy application device 12 may be considered to be off-target when positioned greater than a pre-determined distance from an indicator (e.g., more than 1 cm, 3 cm, 5 cm, etc.) or when not positioned within the boundaries of the indicator (e.g., a circular indicator). The energy application device 12 may be considered to be on-target when positioned less than a pre-determined distance from an indicator (e.g., more than 1 cm, 3 cm, 5 cm, etc.) or when positioned within the boundaries of the indicator (e.g., a circular indicator) or mostly within the boundaries (e.g., at least 75%, at least 90% within). In another embodiment, the energy application device 12 is considered to be off-target or on-target based on a position relative to patient or an absolute position in space compared to an absolute position of the patient.

The indication to the caregiver or user related to on-target or off-target positioning may be one or more of a text message, a light (e.g., a red or green light), a sound or alarm, etc. The indication can also be a haptic effect, such as a vibration pattern of a vibration actuator that is embedded in the energy application device 12 (e.g., the ultrasound probe).

In one example, while scanning around the general area, when the predetermined treatment position is found (either by automated image processing or alignment to an indicator on the skin), the vibration actuator will buzz. The user then learns to find the buzz as they are sweeping around and intuitively move the probe back to the location where the buzz was felt. In another example, different vibration patterns could be used for on-target vs. off-target. Further, the system 10 may also be configured to provide information related to dose length to instruct the patient 70 to hold the energy application device 12 aligned with the predetermined treatment position 46 during the entire length of the dose or until the total dose is higher than a predetermined threshold.

When the energy application device 12 is determined to be off-target, the system 10 may be configured to provide guidance to permit patient-driven steering or repositioning to an on-target position. In an embodiment shown in FIG. 10, when the initial position is determined to be off-target, e.g., via the acquired image 92 (depicted as a spleen image), the system 10 may provide one or more steering arrows 94 or other indicators to direct the patient 70 to steer the energy application device towards alignment with the predetermined treatment position 46, e.g., associated with the image 96 (depicted as a deeper image of the spleen acquired upon patient repositioning of the device 12 and showing blood vessel entry). Such an image may indicate positioning of the energy application device 12 in alignment with the predetermined treatment position 46 for the spleen.

The user interface displayed to the patient 70 may include the arrows with the associated images. Simple feedback of the device position permits the patient to find the predetermined treatment position without interpreting an image that may be difficult for an untrained operator to resolve. The patient may also find the location using automated and support hardware, including holding fixtures and actuators that enable movement of the probe and/or ultrasound focus position without the need for physical/manual manipulation of the probes itself. As discussed herein, a haptic, visual, and/or audio feedback may be activated as the user passes by the right location during some initial sweeps. For example, a beep or other tone may be triggered at on-target locations.

Figure 11:
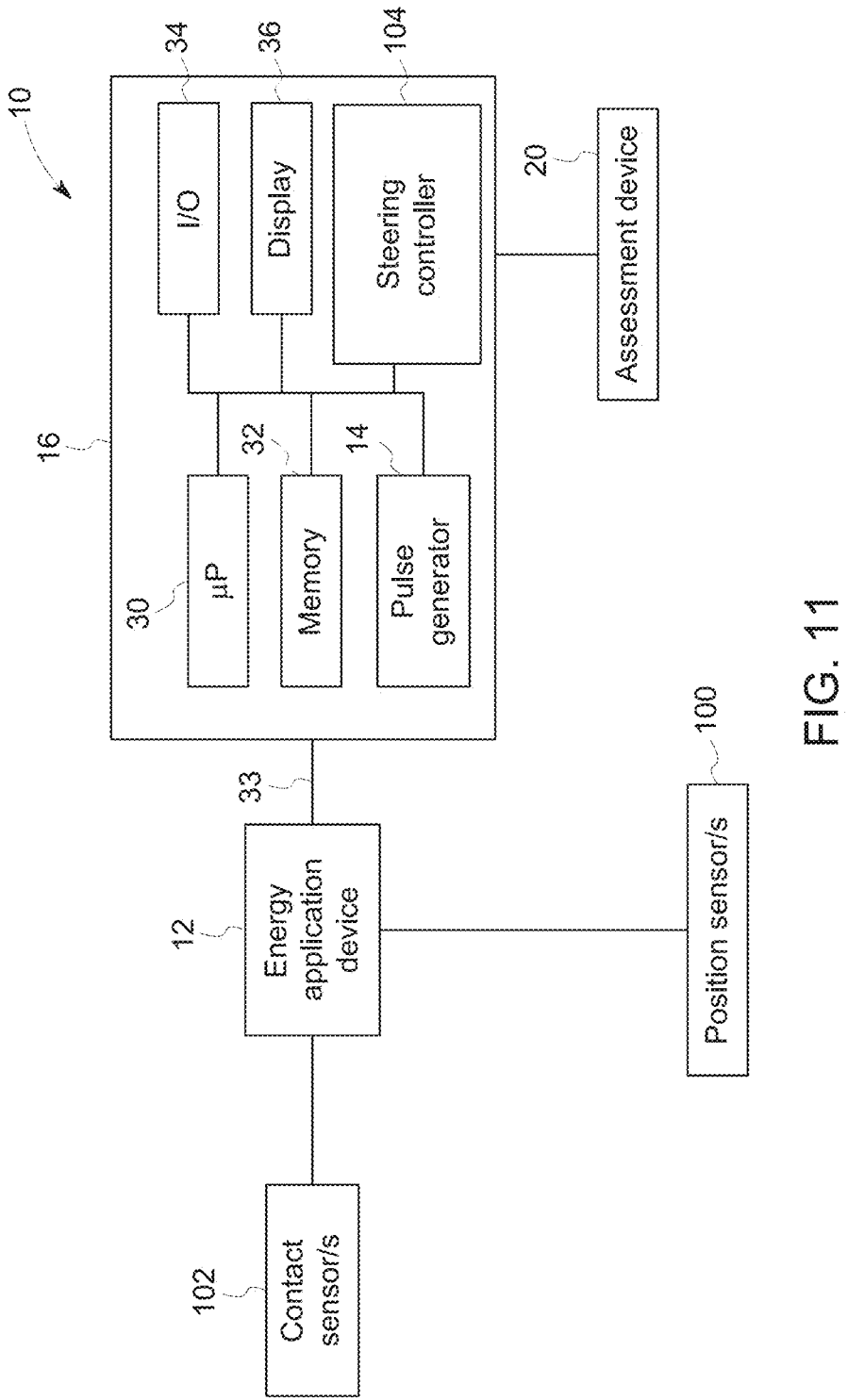
FIG. 11 is a block diagram of a neuromodulation system according to embodiments of the disclosure.

The system 10 may be implemented with position assessment and/or steering capabilities FIG. 11 is a block diagram of a neuromodulation system according to embodiments of the disclosure. The depicted embodiment includes certain features discussed with regard to FIG. 2. Additionally, the system 10 may include one or more position feedback devices integrated in or on the energy application device 12 and configured to generate corresponding position signals indicative of the position of the energy application device 12. The signals may be communicated to the controller 16, which may then process the signals as part of a determination of whether the energy application device 12 is on or off target. The position feedback devices may include sensors 100, which may be any type of position sensor, including optical sensors, cameras, inertial measurement units (IMUs) that track relative motion information from an initial reference, Hall effect sensors, electromagnetic position sensors, etc. Additionally or alternatively, the energy application device 12 may also include one or more contact sensors 102 configured to assess contact of the energy application device 12 with the skin or clothing item of the patient, or associated mechanical fixture. Alternatively, the system 10 may infer through the real-time automated image processing of the acquired anatomical image if the energy application device 12 is sufficiently in contact with the user. The system 10 may be configured to prevent energy application when there is lack of contact or pressure. Additionally or alternatively, the system may also include a steering controller 104 configured to provide instructions to steer the energy application device 12. The steering controller 104 is depicted as part of the controller 16, but may, in other embodiments, be integrated with a steering system of the energy application device 12.

Figure 12:
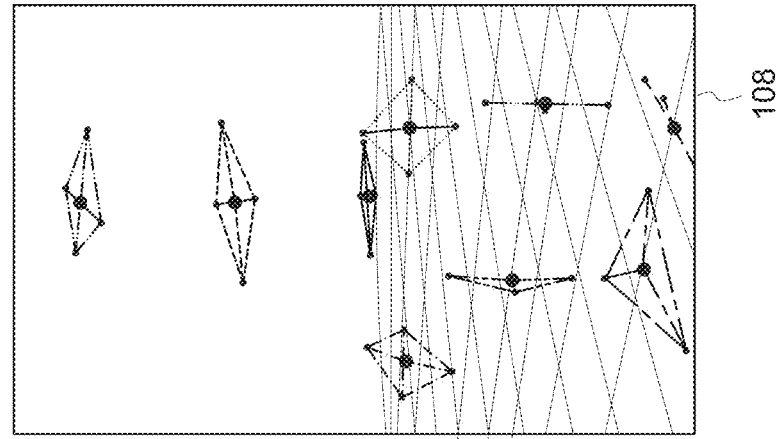
FIG. 12 is a schematic representation of an energy application device including one or more position feedback devices and associated position signals according to embodiments of the disclosure.
Figure 12:
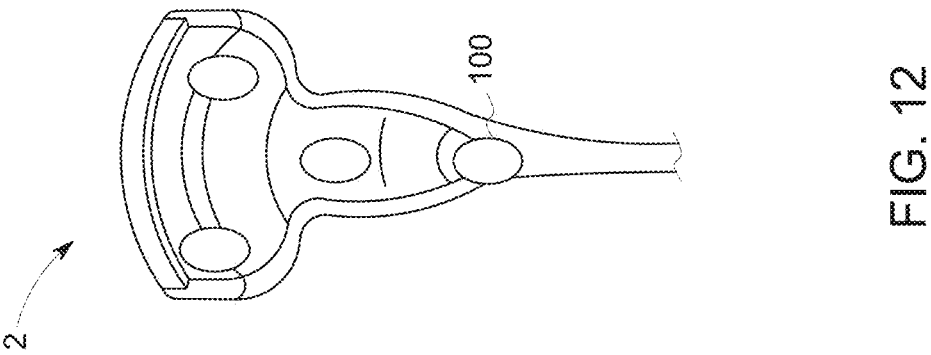
Figure 12:
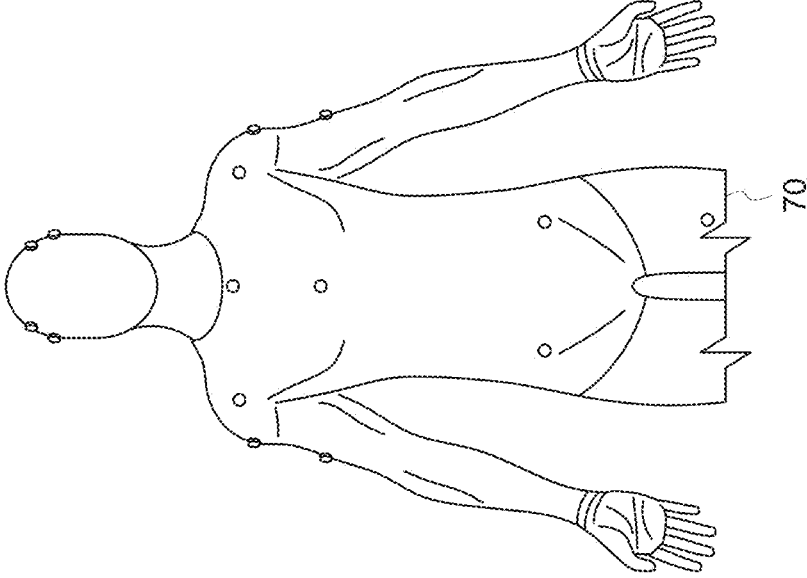

FIG. 12 is a schematic representation of an energy application device including position feedback devices, such as one or more optical position sensors 100 and associated position signals showing camera tracked position according to embodiments of the disclosure. Multiple optical position sensors 100 can be used on probe as well as being positioned on the patient, to know exact location, pitch, and twist of the energy application device 12. In another embodiment, the position sensors 100 may be implemented as sensors 100 tracked by an external electromagnetic Field generator (FG), which induces a small current. Sensors 100 are tracked and depend on distance and angle from FG. In another embodiment, the position sensors 100 may be commercial IMUs or orientation sensors based on accelerometers and gyros directly placed on the energy application device 12. Such sensors may sense change relative to a position, i.e. relative to a skin indicator associated with a predetermined treatment position or pose 46.

Figure 13:
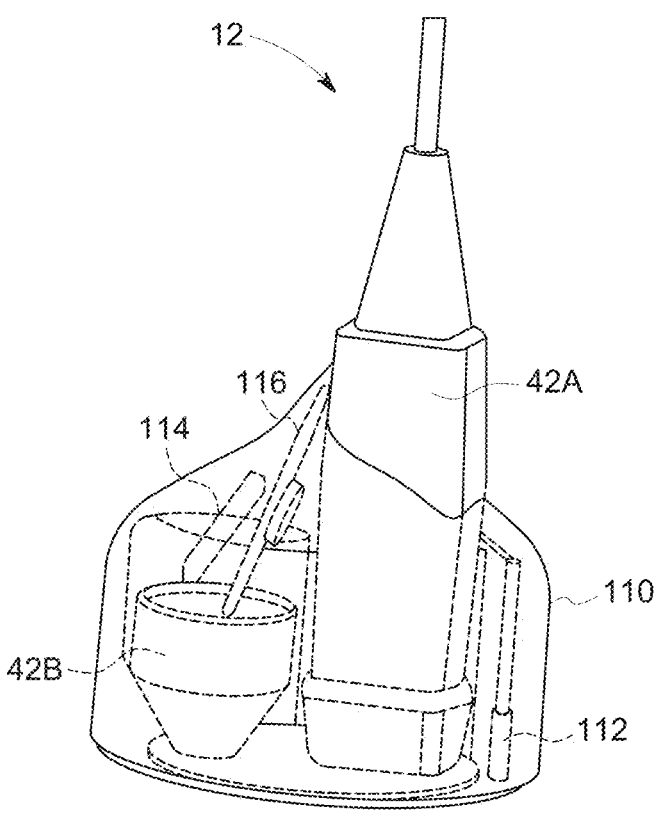
FIG. 13 is a schematic representation of an energy application device including one or more position feedback devices according to embodiments of the disclosure.
Figure 14:
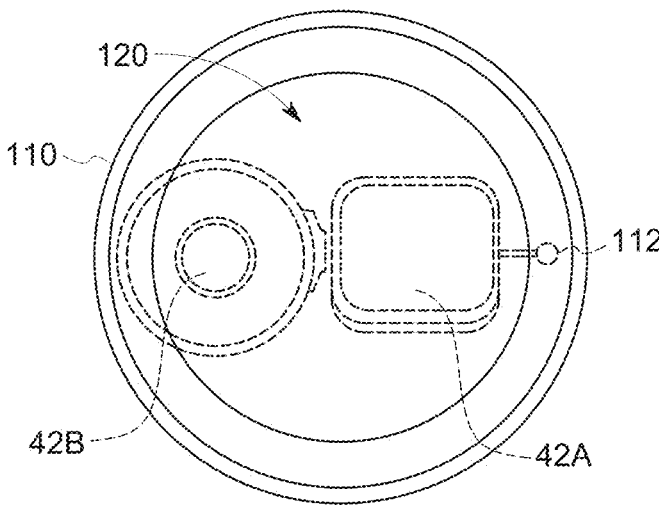
FIG. 14 is a bottom view of the energy application device of FIG. 13.

FIG. 13 is an embodiment of an energy application device 12 including one or more position feedback devices (imaging transducers, positions sensors, cameras, etc.) that provide position information. The energy application device 12 may be provided at least partially within a housing 110 that permits the patient or user to manipulate or position the device 12 on the patient for treatment. The depicted embodiment of the energy application device 12 includes the treatment transducer 42B, e.g., a piezo element (or other ultrasonic actuator), and the imaging transducer 42A within the housing 110 and proximate to one another. The housing 110 may include a camera 112 and associated components, e.g., lens, light source, that are oriented to acquire images from the treatment surface 120 of the energy application device 12, e.g., that are pointed away from the treatment surface 120 to acquire image of the patient's skin or clothing when applied to the patient. The energy application device 12 may include one or more sensors, such as an inertial measurement unit 114 that is configured to provide position and/or tilt or angle data related to the energy application device 12. In some embodiments, the energy application device 12 may include an identification tag, e.g., RFID tag, encoded memory, that provides identification or other calibration information to the controller 16. In one embodiment, the calibration information may include information related to a spacing between the imaging transducer 42A and the treatment transducer 42B to account for any differences between treatment energy based on images acquired. That is, the controller 16 may be configured to adjust a positioning determination for the energy application device 12 to account for the spacing. The energy application device 12 may also include control circuitry to permit transmission of signals to and from the energy application device. FIG. 14 is a bottom view of the energy application device 12 of FIG. 13 showing a treatment surface 120, e.g., an ultrasound treatment surface, of the device 12. The treatment surface 120 of the energy application device 12 may be directly applied to the patient's skin.

It should be understood that other implementations of the energy application device 12 are contemplated. For example, the transducer 42 may be an imaging/therapy transducer 42 designed to image and apply therapy and with one or more sensors 100 embedded within the handle. Further, the camera 112 may be mounted at various positions, e.g., higher up on the handle and not on the treatment surface 120, but closer to the top of the device 12 to facilitate imaging of the skin and temporary tattoo or other indicator. The energy application device 12 may include a processor such that at least a portion of the image processing, targeting, and/or calibration may be performed on the device 12. In addition, the energy application device may include communication circuitry to permit wired or wireless communication with another device, e.g., the controller 16, a mobile device.

Figure 15:
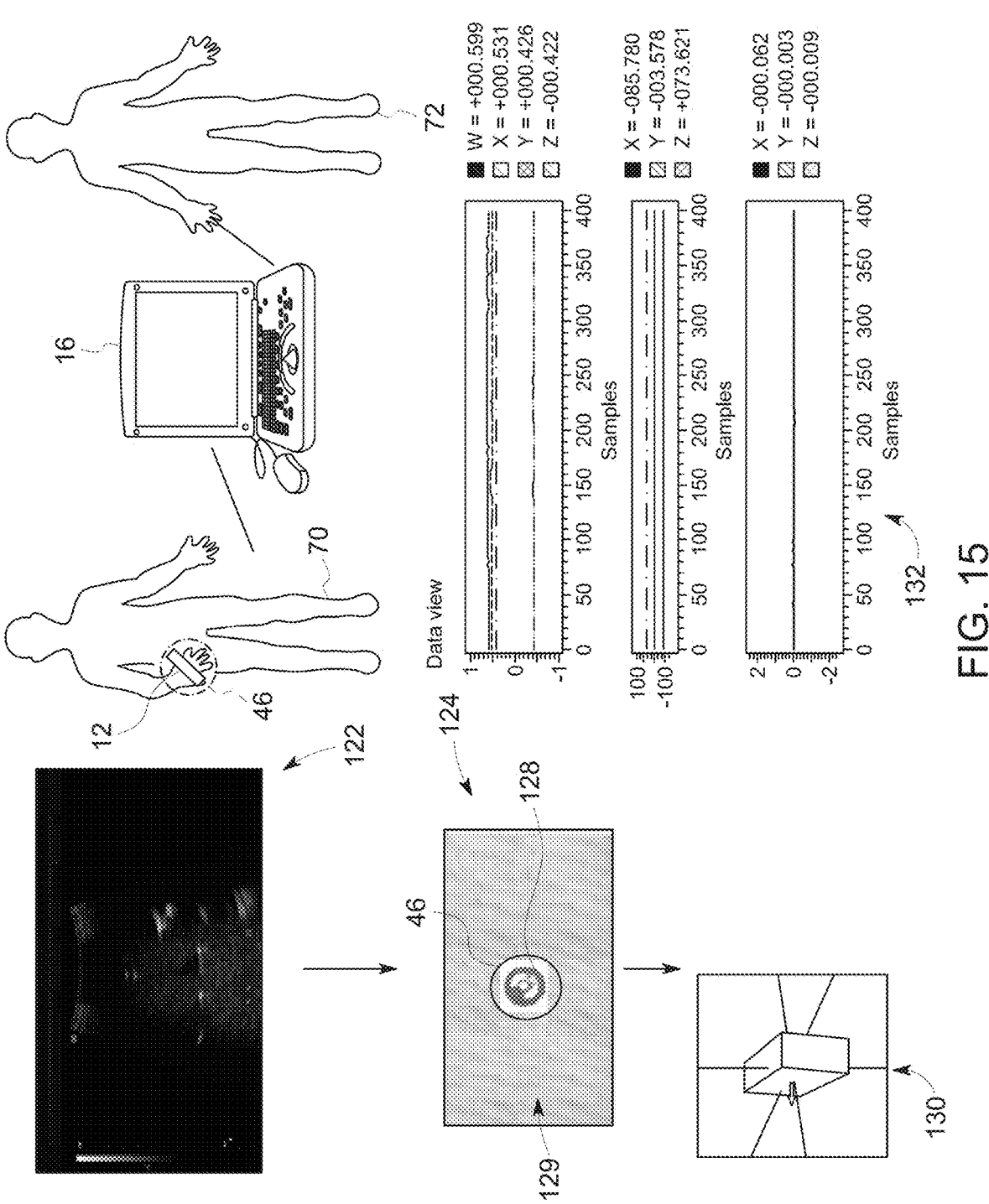
FIG. 15 is a schematic representation of a technique for identifying a predetermined treatment position for an energy application device according to embodiments of the disclosure.

FIG. 15 is a schematic representation of a technique for identifying a predetermined treatment position 46 for an energy application device 12 in conjunction with an expert or physician 72. The depicted technique may be performed at an initiation or establishment of a treatment protocol or as part of a verification of a treatment protocol. At step 122, images are acquired using the energy application device 12 in an imaging mode to locate a region of interest 44 (see FIG. 3) within an internal tissue or structure of the patient 70. The predetermined treatment position 46 is based on a relationship between the external or extracorporeal location of the energy application device 12 on the patient's body and the region of interest 44 corresponding to a focal zone of energy application device 12 when the energy application device 12 is positioned at the predetermined treatment position 46. In other words, the predetermined treatment position 46 corresponds to the location of the energy application device 12 on the patient's body (e.g., in direct contact with the patient's skin) at which the applied energy passes through the patient's skin and reaches the region of interest 44.

The predetermined treatment position 46 may be marked on the patient's skin 129 as shown at step 124 or on the patient's clothing, or through other placement of mechanical fixture on or near the patient. In the depicted embodiment, the predetermined treatment position 46 is marked with a temporary tattoo 128. However, other markers may be used, such as permanent tattoos, stickers, pen markings (visible or fluorescent), etc. The predetermined treatment position 46 then serves as a guide for positioning the energy application device 12 for future treatments as provided herein. The establishment of the predetermined treatment position 46 may also include storing data associated with correct alignment, such as data from a position feedback device. In one embodiment, positioning data from an inertial measurement unit sensor 114 is used to generate a position guide 130 and position data 132 associated with alignment. Deviation from the data (e.g., more than 5% deviation, more than 10% deviation in any direction) may be associated with misalignment or lack of alignment. In another embodiment, the position data may include an ultrasound image or a camera image of the patient.

Figure 16:
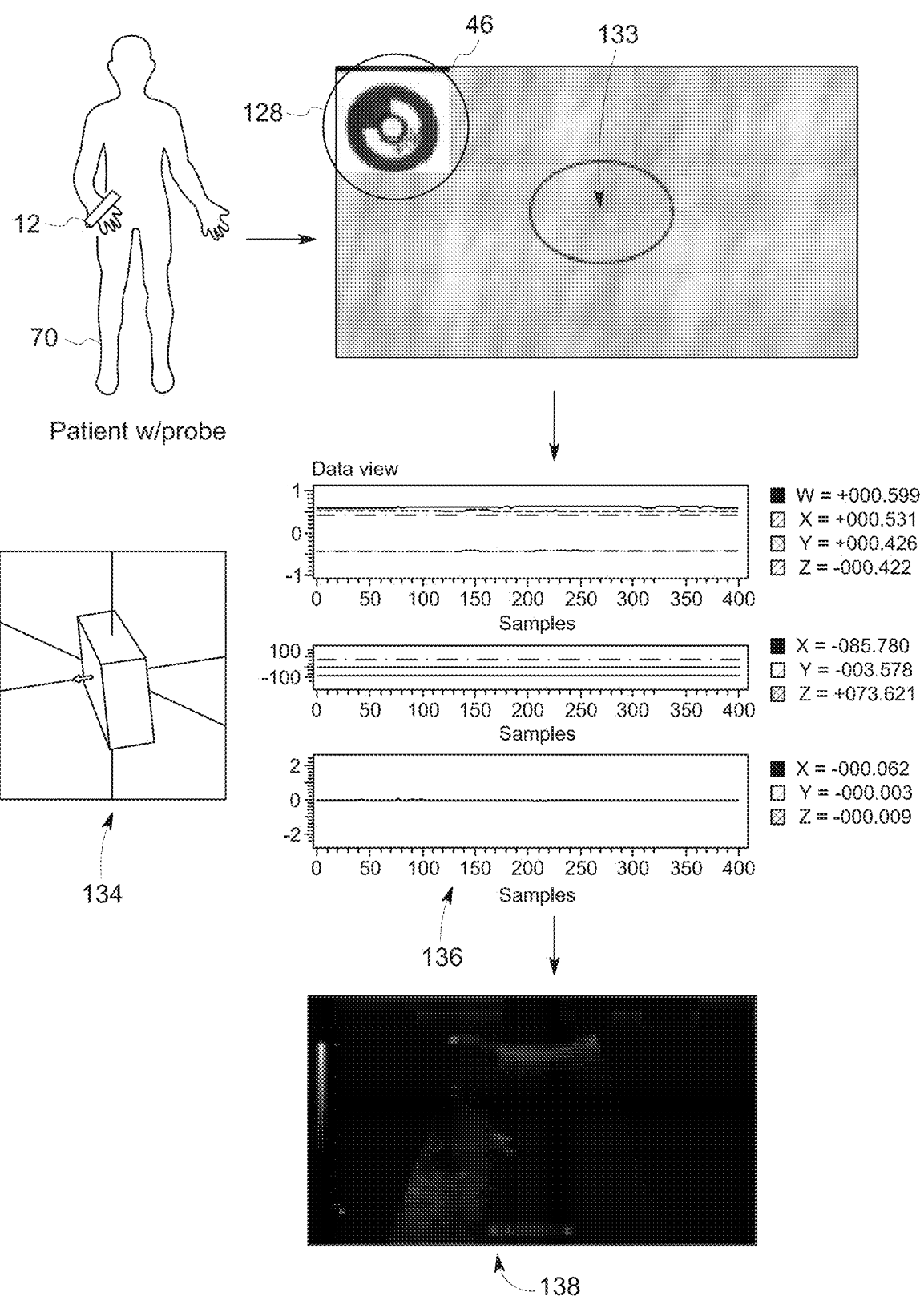
FIG. 16 is a schematic representation of a technique for determining that an energy application device is not positioned at a predetermined treatment position according to embodiments of the disclosure.

FIG. 16 is a schematic representation of an example in which the energy application device 12 is not aligned with a predetermined treatment position 46. For example, the patient 70 may apply the energy application device 12 for at-home treatment. In the example, the energy application device is not positioned on the predetermined treatment position 46, marked with the tattoo 128. Instead, the energy application device 12 is positioned at misaligned position 133. Data is collected from the energy application device 12 at the misaligned position to determine that the energy application device 12 is not aligned. For example, such data may include data from the inertial measurement unit sensor 114 to generate the position information 134, 136 with respect to a defined point. In certain embodiments, the patient 70 may track the position information 134, 136 in real time as the energy application device 12 is repositioned to assess if the misalignment is corrected. The data may also include image data, such as ultrasound image data 138. Such data may be provided to the patient 70 or may be stored by the system 10 for review by skilled personnel or automated analysis software, or for dose calculation as provided herein.

Figure 17:
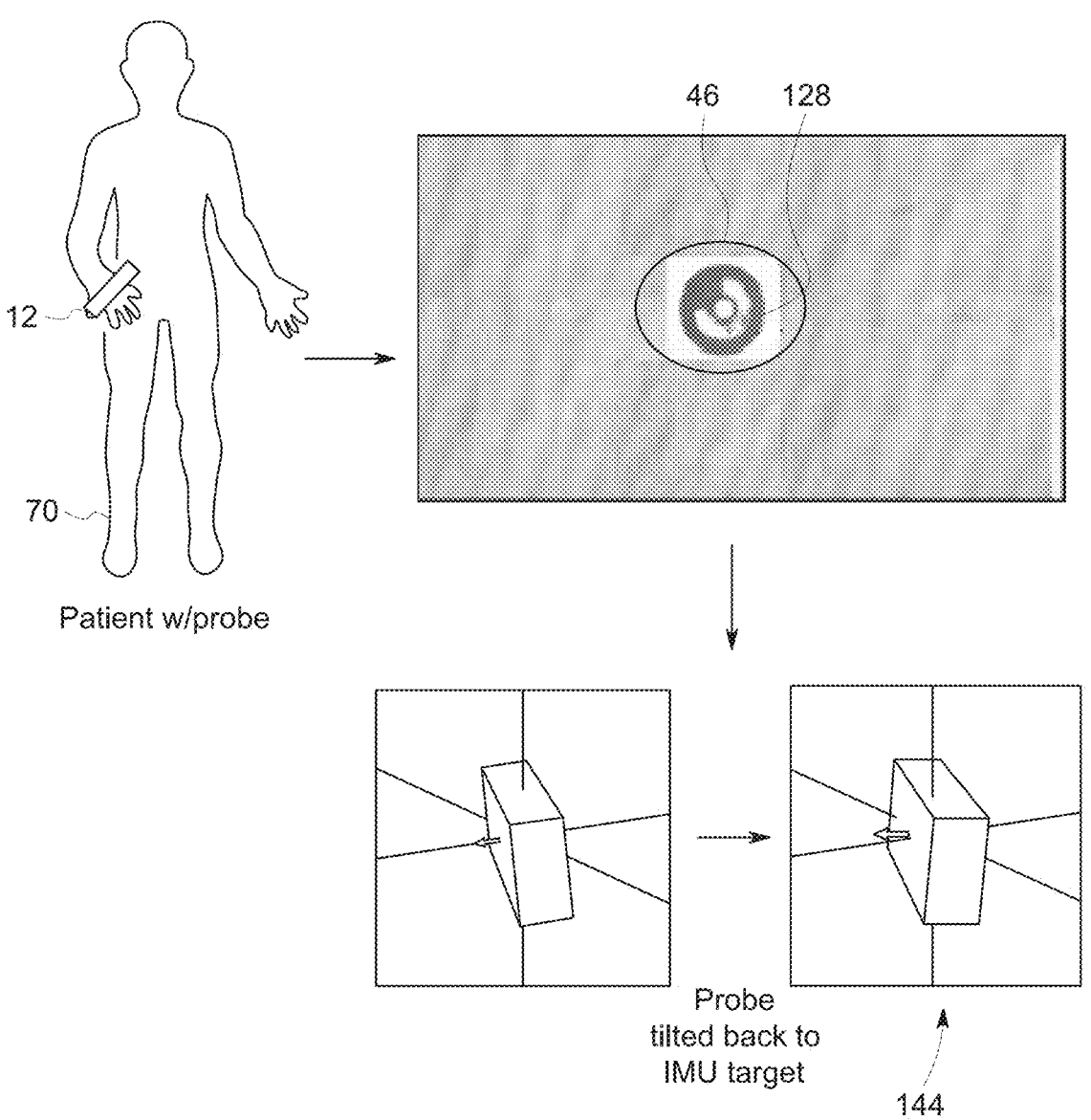
FIG. 17 is a schematic representation of a technique for determining that an energy application device is positioned at a predetermined treatment position according to embodiments of the disclosure.

FIG. 17 is a schematic representation of a technique for determining that an energy application device 12 is aligned at a predetermined treatment position 46. In the depicted embodiment, the energy application device 12 may be positioned at the predetermined treatment position in one axis, but may be incorrectly tilted relative to the skin. Based on the position information 142, the patient 70 may be provided with instructions to tilt the energy application device 12 in a particular direction to perfect the alignment, as indicated with position information 144.

Figure 18:
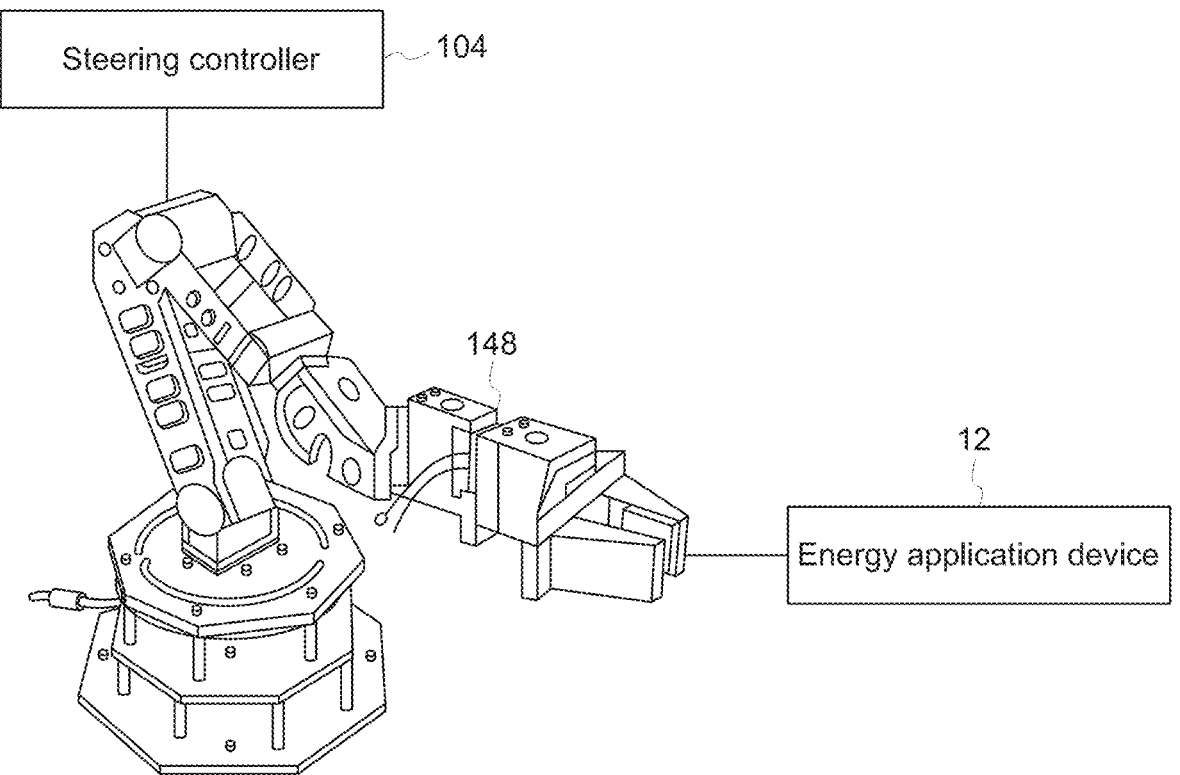
FIG. 18 is a schematic representation of an energy application device coupled to a steering device coupled to a steering controller according to embodiments of the disclosure.

FIG. 18 is a schematic representation of an energy application device 12 coupled to a steering device 148 in turn coupled to a steering controller 104 according to embodiments of the disclosure. The steering device 148 may be a mechanical arm that operates under control of the steering controller 104 to position/reposition the energy application device 12 until aligned with the predetermined treatment position 46. In another example, the device is attached to a belt or garment that the patient straps on over the general target area. Motion stages in the belt align the device 12 to the target position Similar motion control mechanisms could be provided in a ultrasound chair or bench using other types of motion stages.

Figure 19:
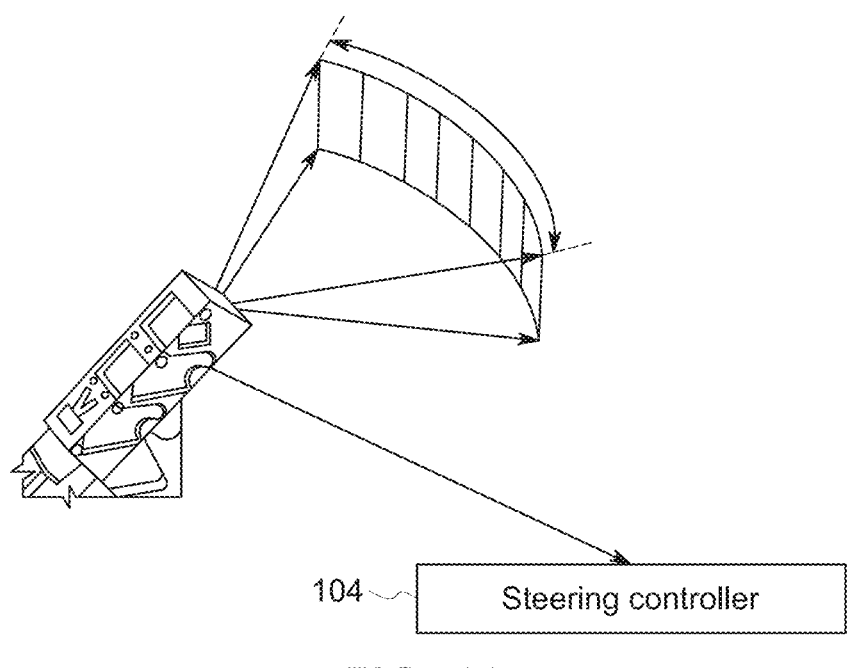
FIG. 19 is a schematic representation of an energy application device including a steerable head coupled to a steering controller according to embodiments of the disclosure.
Figure 20:
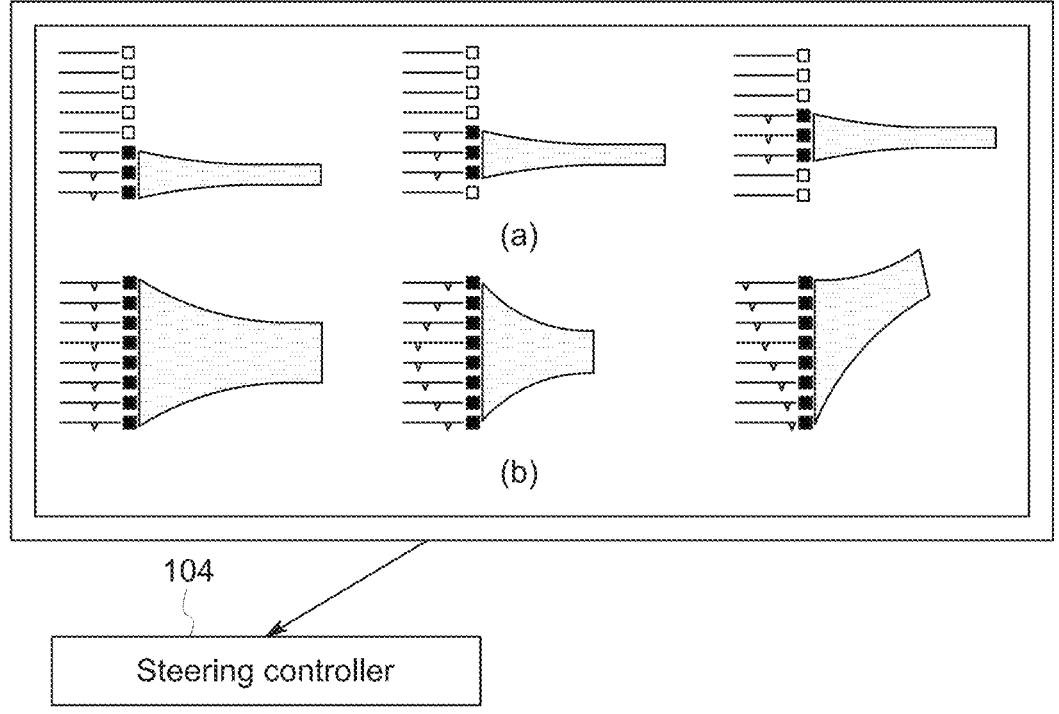
FIG. 20 is a schematic representation of an ultrasound energy application device with beam steering coupled to a steering controller according to embodiments of the disclosure.

In certain embodiments, the system 10 may be configured to complete or optimize a user's general movement of the energy application device near a predetermined treatment position 46. FIG. 19 is a schematic representation of an energy application device 12 including a steerable head coupled to a steering controller 104 according to embodiments of the disclosure. That is, additionally or alternatively to steering the entire device 12, the steering controller 104 may be configured to manipulate the head, e.g., an ultrasound probe head, to perform fine positioning. FIG. 20 is a schematic representation of an ultrasound energy application device 12 with beam steering coupled to a steering controller 104 according to embodiments of the disclosure. That is, rather than or in addition to repositioning all or part of the device 12, the energy application device 12 may also be configured to use beam steering to redirect the beam closer to the region of interest 44.

Figure 21:
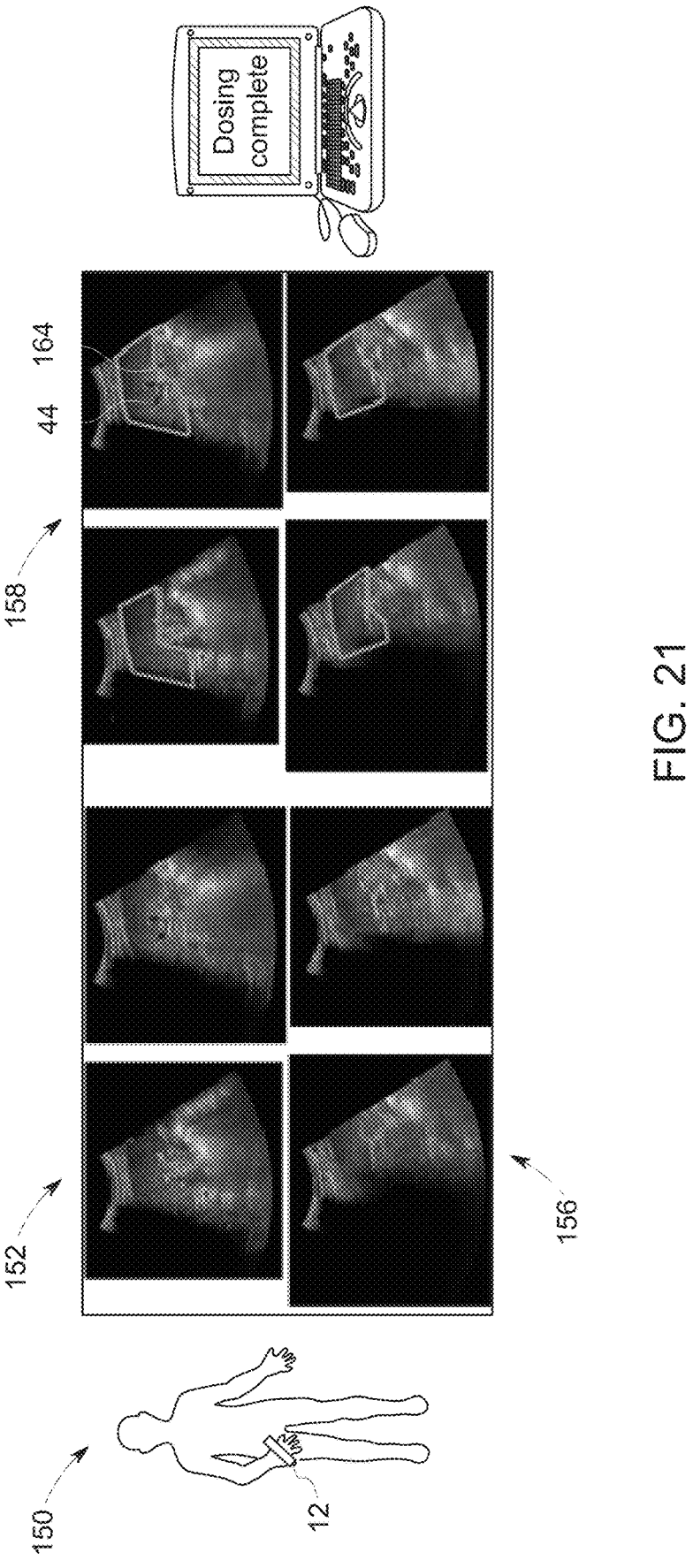
FIG. 21 is a schematic representation of an sweeped energy application technique according to embodiments of the disclosure.

In addition to embodiments in which the energy application device 12 is aligned with the predetermined treatment position 46, FIG. 21 is a schematic representation of a diffuse energy application technique according to embodiments of the disclosure. The patient 70 scan or sweep or move the energy application device 12 around a general area (step 150) while the system 10 acquires information (step 152) about the area swept (e.g., images 156). The general area may be on or around the predetermined therapy position previously identified by a caregiver or expert as discussed herein. The system 10 may determine the volume and/or time during the sweep that is associated with target dosing of the region of interest 44, e.g., using image segmentation (areas 164), during the sweep. Once the total dose is at a predetermined level, the system 10 may provide an indication of complete dose to indicate that the patient should stop sweeping. In certain embodiments, achieving the total dose triggers a shutoff of the energy application device 12. Such methods may be appropriate if the tissue surrounding the region of interest can be stimulated with limited side effects. Further, the system 10 may be configured to provide feedback mechanisms to let patient 70 know if they are not "accumulating applied energy" fast enough (i.e. instructions to sweep in new position). In addition, in certain embodiments, the system 10 may trigger a shutoff to the energy application deice 12 if dosing of off-target sites accumulates to levels above a threshold. The disclosed sweeping may be performed with an unfocused or soft focused ultrasound to provide a wider sweep.

In another embodiment, a scanning process includes triggering the therapy beam on/off based on real-time alignment. During scanning, the energy application device 12 is configured to continuously image at imaging power levels to find alignment in the image with the predetermined target and/or continuously processing the camera and transducer (e.g., ultrasound image) data to find alignment with the skin indicator. In another implementation, the therapy beam is intermittently activated during the sweep when the alignment is correct and disabled when alignment is incorrect while intermittently counting up the dose up to a target. In another embodiment, the system is configured such that the user holds the energy application device 12 still in a target position for a period of time (i.e. 1 sec) before activating the therapy beam, where the user is supposed to remain still during the application of therapy. User movement is detected either by real-time processing of imaging ultrasound, inertial measurement units, or camera data, and the therapy beam is immediately deactivated. The cycle continues of therapy beam activation/deactivation until accumulation of dose reaches the target.

Figure 22:
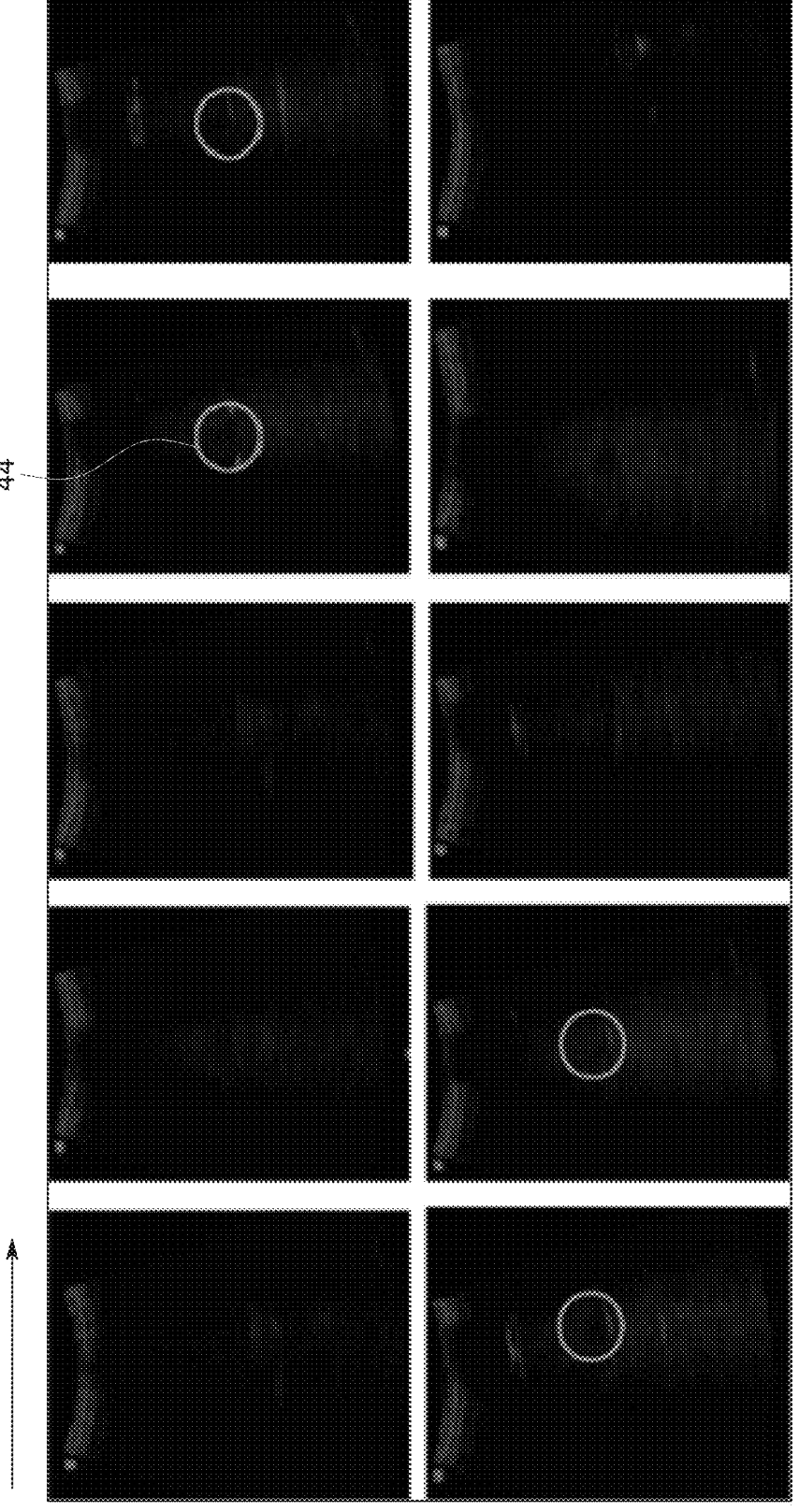
FIG. 22 is a panel of images acquired from a sweeped energy application technique.
Figure 23:
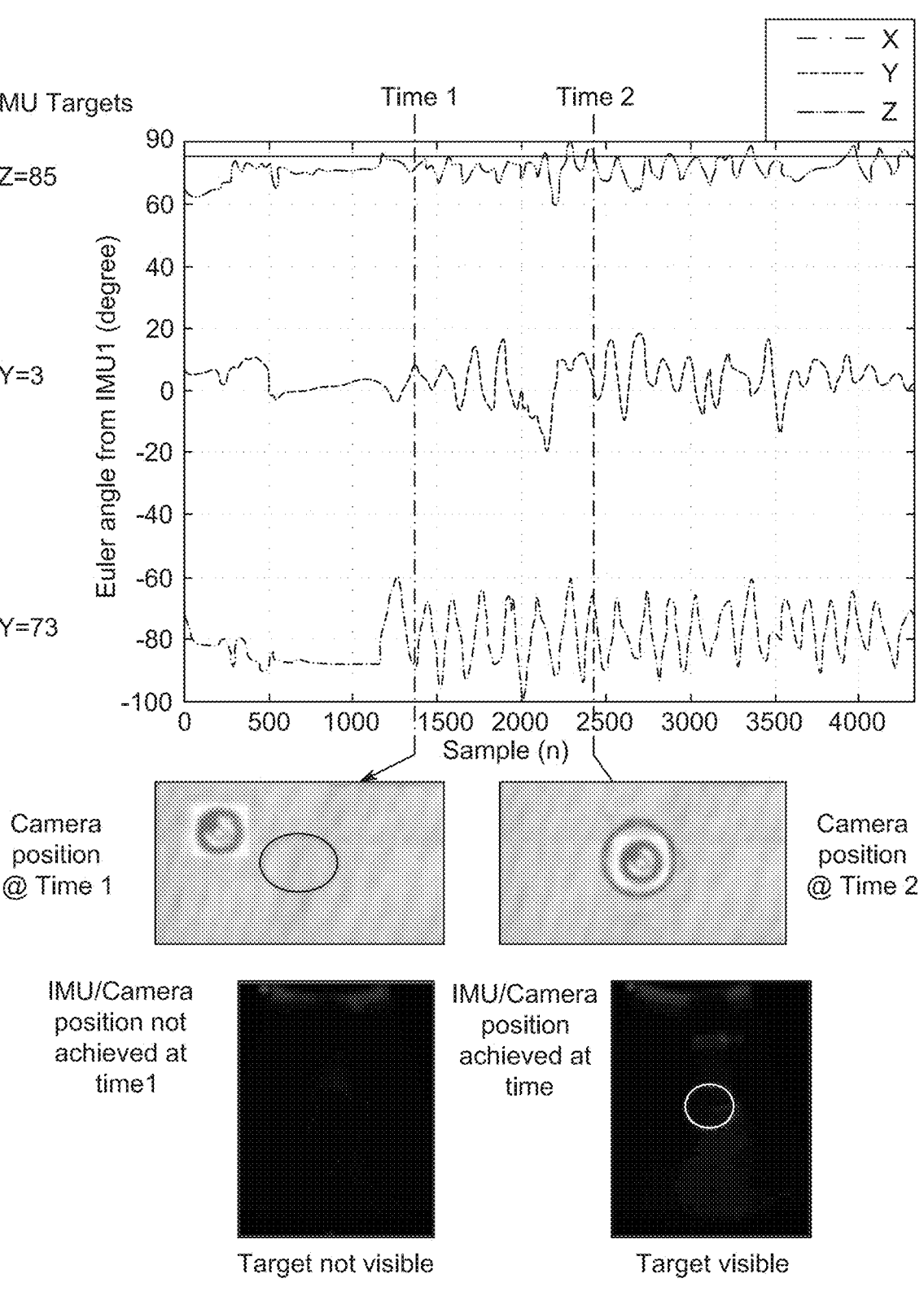
FIG. 23 is an example of energy application device position data that may be used in conjunction with the sweeped energy application technique to determine a total dose according to embodiments of the disclosure.

FIG. 22 shows an example of a panel of images associated with a sweeping technique indicating the region of interest. The determination of the dose applied to the region of interest 44 as well as to areas outside of the region of interest 44 may be determined based at least in part on position feedback from sensors 100 associated with the energy application device 12 as shown in FIG. 23. In the depicted example, the feedback may be based on a signal from one or more inertial measurement units positioned on or in the energy application device 12. The feedback may also be based on an optical sensor, e.g., a camera 112, of the energy application device 12 that acquires data from the patient's skin to generate position information. In one embodiment, the data is indicative of a position of a tattoo 126 or other sensor-discernible marker relative to the energy application device. Based on the position of the energy application device over a time window, a determination of the dose applied to the region of interest 44 may be made. The dose may be considered to be accumulating at times when the energy application device 12 is determined to be in position on the patient as determined via the camera 112 and/or the sensors 100. The dose may be considered not to be accumulating at times when the energy application device 12 is determined not to be in position on the patient as determined via the camera 112 and/or the sensors 100. When the energy application device 12 is partially in position, the dose may be considered to be a partial dose. Tracking the total dose to the region of interest 44 over the treatment time window permits the system to provide indications of the total dose or an achieved target dose. Further, the total dose to the region of interest 44 may be used as feedback by the controller 16 to control operation of the energy application device 12. When the target dose to the region of interest is achieved, the controller 16 may switch off the energy application from the energy application device 12.

Figure 24:
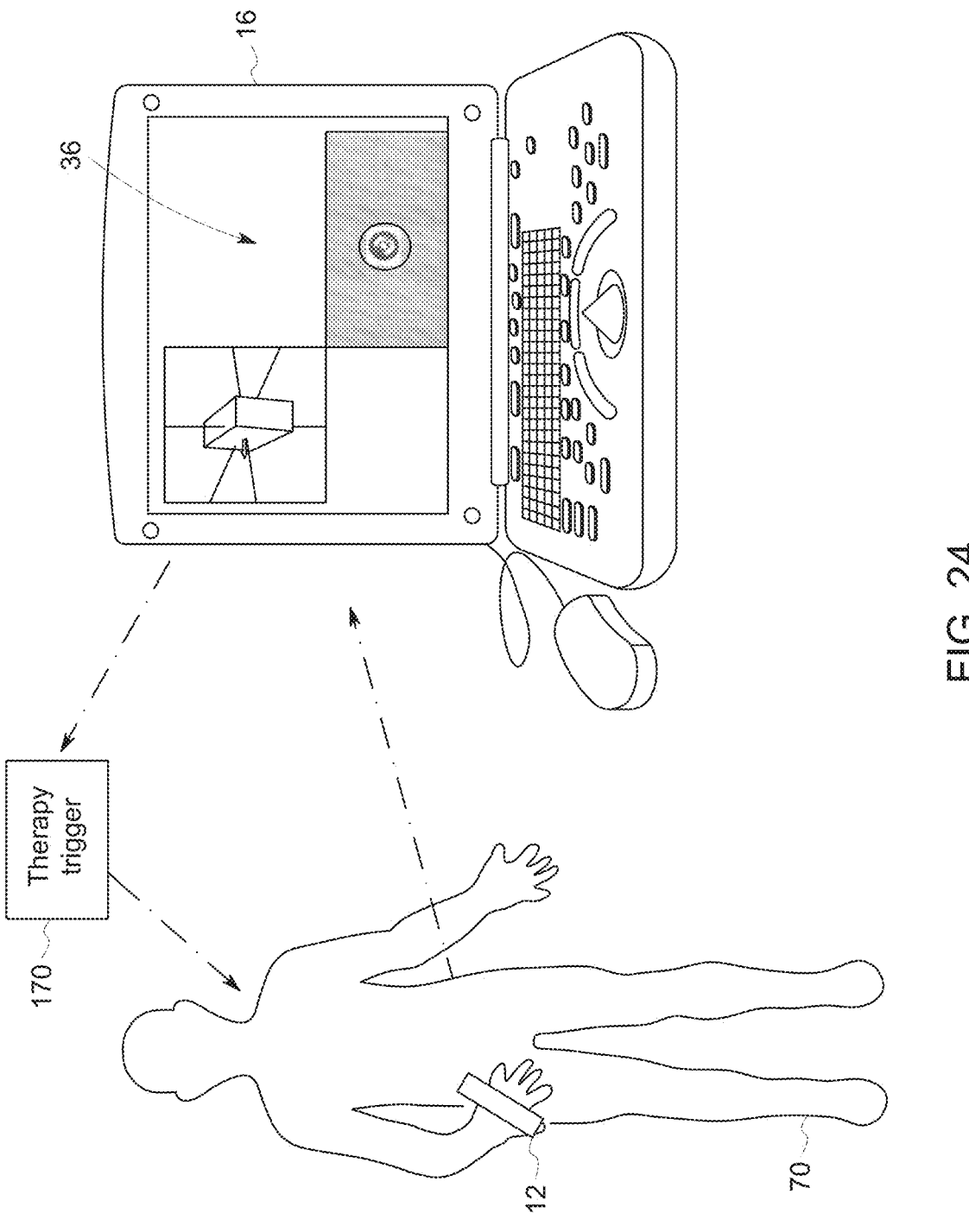
FIG. 24 is an example of a user interface of a system including position feedback according to embodiments of the disclosure.

In another embodiment, position data may be used to provide feedback to the patient 70 related to the position of the energy application device 12. FIG. 24 shows the display 36 of the controller 16 providing a user interface including suggested positioning of the energy application device 12, e.g., via colors, arrows, images, or other indicators (audio indicators, light indicators). In certain embodiments, the energy application device 12 may include or be implemented in conjunction with haptics that would guide the unskilled or relatively untrained operator to move up/down/left/right by haptic feedback. Haptics or audio feedback also may be used to provide yes/no guidance using a tone/absence of a tone or haptic/absence of a haptic to indicate positioning of the energy application device 12. In such embodiments, the use of a display for guidance may be optional. The controller 16 may also be configured to only trigger therapy (block 170) when the energy application device 12 is correctly positioned.

Figure 25:
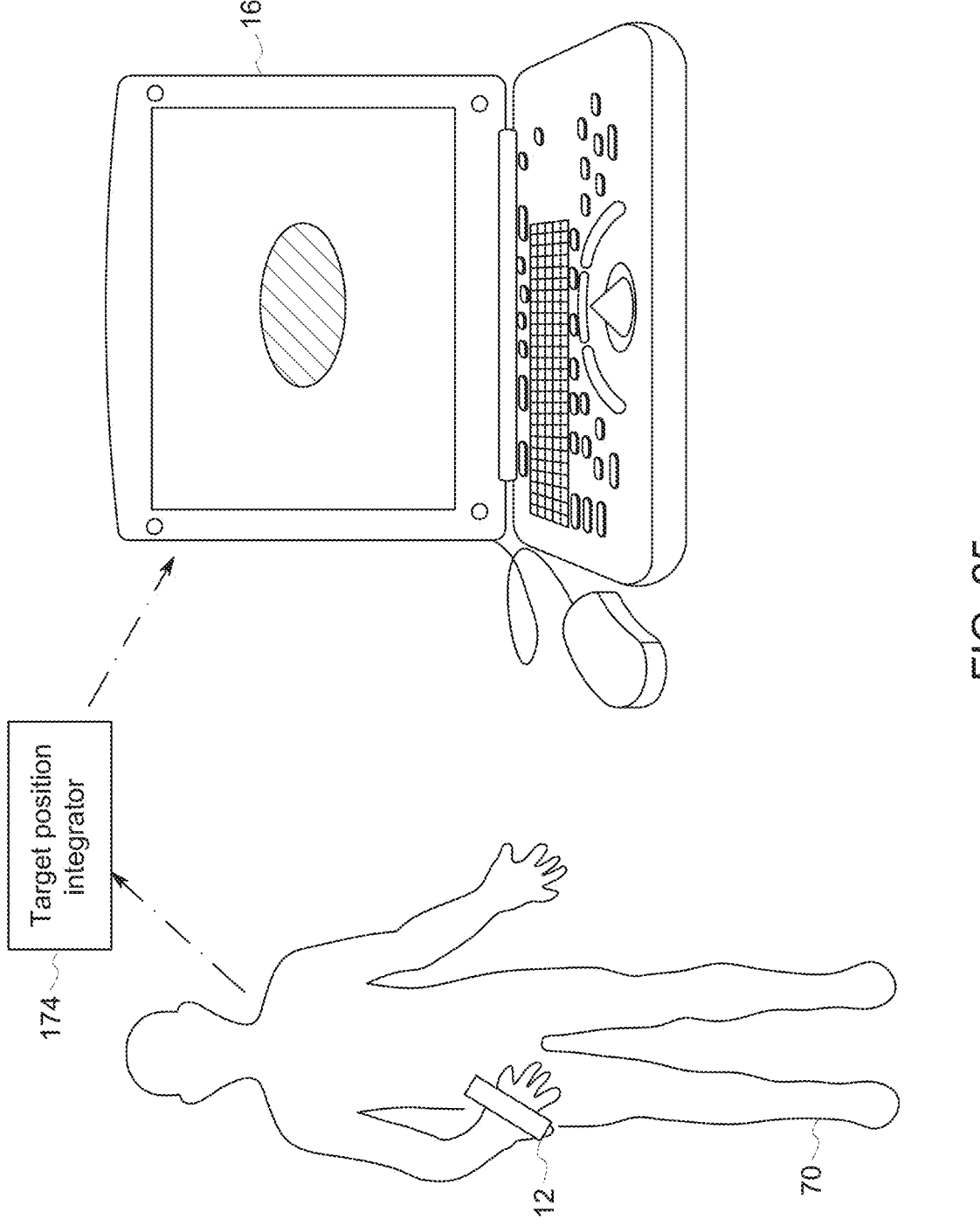
FIG. 25 is an example of a user interface of a system including dose feedback according to embodiments of the disclosure.

FIG. 25 shows an embodiment in which the controller 16 provides an indicator via the display 36 relating to the total dose. For example, a shape may fill in as the dose is accumulating. Further, the display 36 may provide a user interface that indicates that the energy application device 12 is correctly positioned to provide the dose to the region of interest 44. It should be understood that the user interface may alternatively or additionally provide information such as acquired images, segmentation data, sensor data, etc.

Figure 26:
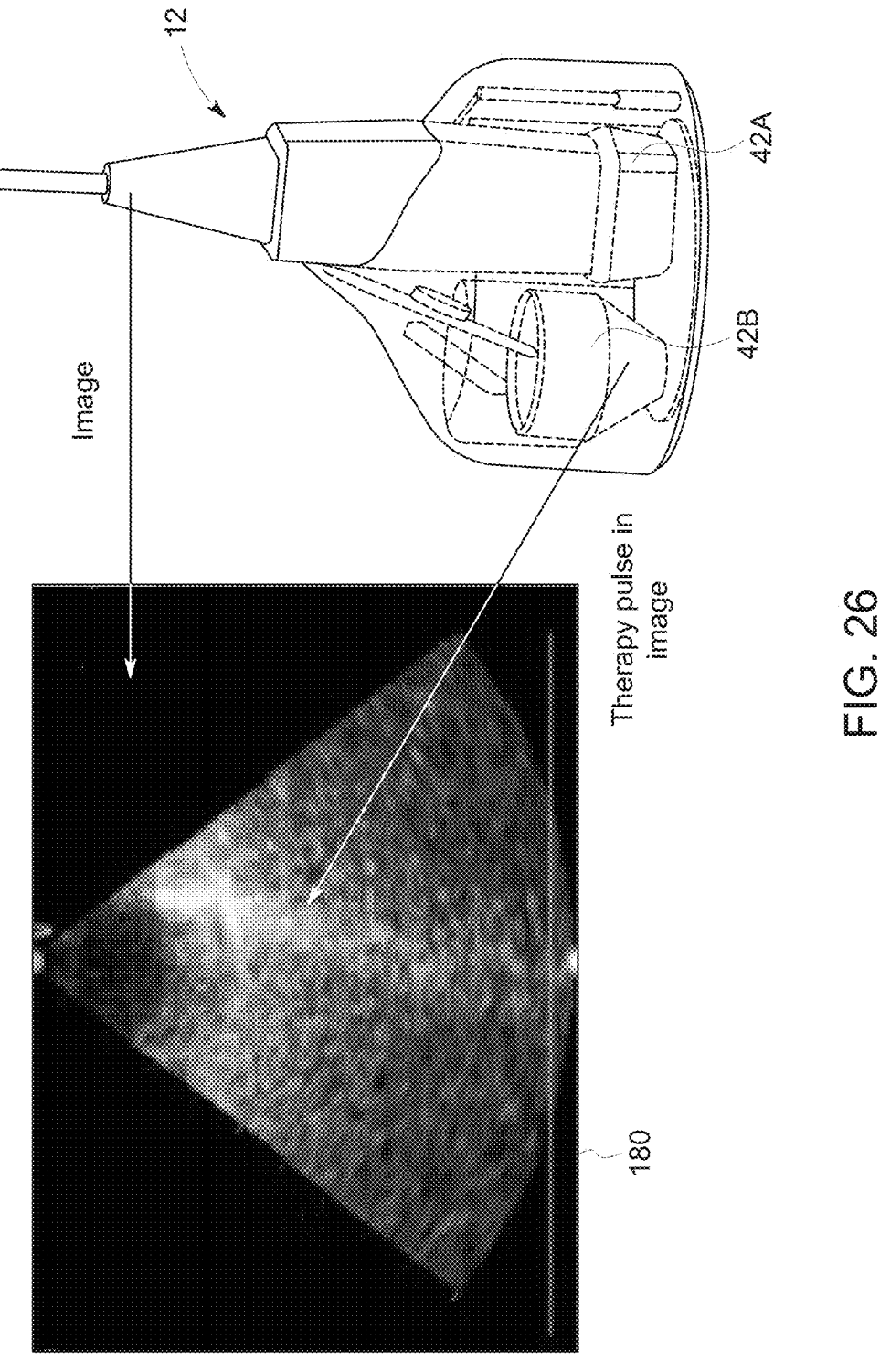
FIG. 26 is an example of a therapy pulse visualization and recording technique using an energy application device according to embodiments of the disclosure.

The application of therapeutic pulses to the tissue may result in resolvable images changes that may be viewed during therapy. For example, the targeted tissue may move, pulse, or expand in response to the applied energy. FIG. 26 is an example of the energy application device 12 being used to simultaneously (or nearly simultaneously) provide therapy energy via the therapy transducer 42B and to acquire images (e.g., image 180) via the imaging transducer 42A during the treatment. In one embodiment, the frequencies of the imaging transducer 42A and the therapy response and/or treatment transducer 42B are matched to permit acquisition of images indicative of therapy effects. Further, the dynamic range of the imaging probe is adjusted to target the ultrasound effects to tissue. The energy pulses may be timed to be relatively quick to permit resolution of tissue rebound in the images and not continuously moving tissue. Calibration at lower non-therapeutic pulses may be performed before therapeutic energy is applied.

Mechanisms of Targeted Physiological Outcomes

The present techniques relate to targeted modulation of synapses at axon terminals in a tissue via a direct application of energy by an energy source to cause a change that results in a measurable targeted physiological outcome (e.g., a change in a circulating molecule concentration or a suite of concentrations changes forming a characteristic physiological profile). The targeted synapses may include axoextracellular synapses formed between presynaptic axon terminals and postsynaptic non-neuronal cells. In addition, while certain disclosed embodiments are discussed in the context of axoextracellular synapses, it should be understood that the axon terminals may form axosecretory, axosynaptic, axosomatic or axoextracellular synapses, and that additionally or alternatively, these synaptic types are contemplated as being selectively modulated, as provided herein. Further, certain axon terminals may terminate in interstitial or body fluid that may also experience neurotransmitter release and/ or axonal/terminal activation as a result of the modulation. The disclosed synapses may be modulated to alter an activity in the synapses, e.g., a release of neurotransmitters from the presynaptic axon terminals, as a result of the energy application. Accordingly, the altered activity may lead to local effects and/or non-local (e.g., systemic) effects to cause the overall profile of physiological changes associated with the desired or targeted physiological outcome. The present techniques permit energy to be focused in a targeted manner on a volume of tissue that includes certain axon terminals to preferentially directly activate the targeted axon terminals to achieve desired targeted physiological outcomes. In this manner, the targeted axon terminals within a region of interest are activated while, in certain embodiments, axon terminals in the same organ or tissue structure but that are outside of the region of interest are not activated. Because organs and tissue structures may include different types of axon terminals that form synapses with different types of postsynaptic non-neuronal cells, the region of interest may be selected that includes particular types of axon terminals that, when activated, yield the desired targeted physiological outcome. Accordingly, the modulation may target a specific type of axon terminal on the basis of the presynaptic neuron type, the postsynaptic cell type, or both. As provided herein, energy is applied to a region of interest in a patient's body in an amount effective to induce neuromodulation of one or more nerve pathways, e.g., the targeted physiological outcome. The effective amount may be assessed as generally disclosed herein, such as via an assessment device. The effective amount may also be applied according to one or more modulation parameters as provided herein.

For example, in one embodiment, the one or more nerve pathways may include an axon terminal forming an axoextracellular synapse with a resident (i.e., tissue-resident or non-circulating) liver, pancreatic, or gastrointestinal tissue cell. That is, the axoextracellular synapse is formed at a junction between an axon terminal and a nonneuronal cell or interstitial or body fluid. Accordingly, the application of energy leads to modulation of function in the region of interest. However, it should be understood that, based on the population of axon terminal types and the characteristics of the presynaptic neuron type and postsynaptic cells (e.g., immune cells, lymph cells, mucosal cells, muscle cells, etc.) of the axoextracellular synapse, different targeted physiological effects may be achieved. Accordingly, applying energy to a region of interest in a tissue of a subject may activate axon terminals of one or more nerve pathways and their associated axoextracellular synapse within the region of interest while untargeted axon terminals (and associated synapses) outside of the region of interest may be unaffected. However, because modulation may result in systemic effects, untargeted axon terminals outside of the region of interest may experience certain systemic changes as a result of the activation of the axon terminals within the region of interest. As provided herein, preferential activation or direct activation may refer to the cells or structures (e.g., synapses) that experience direct application of energy (e.g., the energy is applied directly to the cells or structures) and are within a region of interest. For example, axon terminals, axoextracellular synapses, and/or postsynaptic non-neuronal cells or interstitial or body fluid within the region of interest may directly experience the applied energy as provided herein. Preferential or direct activation may be considered in contrast to areas outside of a region of interest that do not experience direct energy application, even if such areas nonetheless undergo physiological changes as a result of the energy application. Further, in some embodiments, preferential activation may include applying a relatively larger dose of neuromodulating energy to a particular region of interest while areas outside of the region of interest receive relatively smaller doses.

The human nervous system is a complex network of nerve cells, or neurons, found centrally in the brain and spinal cord and peripherally in the various nerves of the body. Neurons have a cell body, dendrites and an axon. A nerve is a group of neurons that serve a particular part of the body. Nerves may contain several hundred neurons to several hundred thousand neurons. Nerves often contain both afferent and efferent neurons. Afferent neurons carry signals to the central nervous system and efferent neurons carry signals to the periphery. A group of neuronal cell bodies in one location is known as a ganglion. Electrical signals generated in the nerves (e.g., via stimulation, which may be intrinsic or externally applied) are conducted via neurons and nerves. Neurons release neurotransmitters at synapses (connections) adjacent to a receiving cell to allow continuation and modulation of the electrical signals. In the periphery, synaptic transmission often occurs at ganglia.

The electrical signal of a neuron is known as an action potential. Action potentials are initiated when a voltage potential across the cell membrane exceeds a certain threshold. This action potential is then propagated down the length of the neuron. The action potential of a nerve is complex and represents the sum of action potentials of the individual neurons in it. The junction between the axon terminals of a neuron and the receiving cell is called a synapse. Action potentials travel down the axon of the neurons to its axon terminal, the distal termination of the branches of an axon nerve that forms a presynaptic ending or a synaptic terminal of the nerve fiber. The electrical impulse of the action potential triggers migration of vesicles containing neurotransmitters to a presynaptic membrane of the presynaptic axon terminal and ultimately the release of the neurotransmitters into a synaptic cleft (e.g., the space formed between the presynaptic and the postsynaptic cell) or the axoextracellular space. A synapse that reaches a synaptic terminal to convert the electrical signal of the action potential to a chemical signal of neurotransmitter release is a chemical synapse. Chemical synapses may be contrasted with electrical synapses in which the ionic currents flowing into a presynaptic axon terminal can cross the barrier of the two cell membranes and enter a postsynaptic cell.

The physiological effect of the action potential is mediated by ion movement across a cell membrane. Neurons actively maintain a resting membrane potential via ion pumps that facilitate movement of ions such as Na+, K+, and Cl– through the neuronal membrane. Different types of neurons may maintain different resting potentials, e.g., –75 mV to –55 mV. An action potential is generated by an influx of ions, i.e., a movement of charge to generate a large deviation in the membrane potential that is associated with a temporary rise in voltage across the membrane, e.g., a rise to a membrane potential in a range of 30-60 mV. The action potential in an individual neuron may be initiated in response to a neurotransmitter release from a presynaptic (e.g., upstream) neuron, which in turn results in receptor binding at the postsynaptic cell and a cascade of events which leads to an influx of ions and membrane depolarization that results in an action potential that is propagated through the nerve.

Synapses may be located at a junction between two neurons, which permits an action potential to be propagated down a nerve fiber. However, axon terminals may also form synapses at the junctions between neurons and non-neuronal cells or may terminate at interstitial fluid or body fluid. Examples of synapse types are synapses with immune cells at a neuroimmune junction, synapses with resident sensory cells within an organ, or synapses with gland cells. Release of neurotransmitters into a synaptic cleft and binding to receptors in a postsynaptic membrane of a postsynaptic cell results in downstream effects that are dependent on the nature of the presynaptic neuron and the specific neurotransmitters released as well as the nature of the postsynaptic cell, e.g., types of available receptors of the postsynaptic cell. In addition, an action potential may be excitatory or inhibitory. An excitatory postsynaptic action potential is a postsynaptic potential that makes the postsynaptic neuron more likely to fire or release a subsequent action potential while an inhibitory postsynaptic action potential is a postsynaptic potential that makes the postsynaptic neuron less likely to fire or release a subsequent action potential. Further, several neurons may work together to release neurotransmitters in concert that trigger downstream action potentials or inhibit downstream action potentials.

Neuromodulation is a technique in which energy from an external energy source is applied to certain areas of the nervous system to activate or increase the nerve or nerve function and/or block or decrease the nerve or nerve function. In certain neuromodulation techniques, one or more traditional electrodes are applied at or near target nerves, and the application of energy is carried through the nerve (e.g., as an action potential) to cause a physiological response in areas of the downstream of the energy application site. However, because the nervous system is complex, it is difficult to predict the scope and eventual endpoint of the physiological response for a given energy application site. In one example, stimulation of axon terminals releases neurotransmitter/neuropeptide or induces altered neurotransmitter release in a vicinity of neighboring non-neuronal cells such as secretory or other cells and modulates cell activity of the neighboring or nearby non-neuronal cells, including the postsynaptic cells.

Benefits of the present techniques include local modulation at the region of interest of the tissue to achieve targeted physiological outcomes that may be used to assess a patient condition. Further, the local modulation may involve direct activation of a relatively small region of tissue (e.g., less than 25% of a total tissue volume) to achieve these effects. In this manner, the total applied energy is relatively small to achieve a desired targeted physiological outcome. In certain embodiments, the applied energy may be from a non-invasive extracorporeal energy source (e.g., ultrasound energy source, mechanical vibrator). For example, a focused energy probe may apply energy through a subject's skin and is focused on a region of interest of an internal tissue. Such embodiments achieve the desired targeted physiological outcome without invasive procedures or without side effects that may be associated with other types of procedures or therapy.

In certain embodiments, techniques for neuromodulation are provided in which energy from an energy source (e.g., an external or extracorporeal energy source) is applied to axon terminals and/or surrounding/supporting tissue in a manner such that the induced targeted physiological outcome, for example, neurotransmitter release, at the site of focus of the energy application, e.g., the axon terminals, is triggered in response to the energy application and not in response to an action potential. That is, the application of energy directly to the axon terminals acts in lieu of an action potential to facilitate neurotransmitter release into a neuronal junction (i.e., synapse) with a non-neuronal cell. The application of energy directly to the axon terminals further induces an altered neurotransmitter release from the axon terminal within the synapse (e.g., axoextracellular synapse) into the vicinity of neighboring non-neuronal cells, and/or activation of sensory pathways that modulate activity in other remote (but specific) areas of the body. In one embodiment, the energy source is an extracorporeal energy source, such as an ultrasound energy source or a mechanical vibrator. In this manner, non-invasive and targeted neuromodulation may be achieved directly at the site of energy focus rather than via stimulation at an upstream site that in turn triggers an action potential to propagate to the downstream site target and to activate downstream targets.

In certain embodiments, the target tissues are internal tissues or organs that are difficult to access using electrical stimulation techniques with electrodes. Contemplated tissue targets include gastrointestinal (GI) tissue (stomach, intestines), muscle tissue (cardiac, smooth and skeletal), epithelial tissue (epidermal, organ/GI lining), connective tissue, glandular tissues (exocrine/endocrine), etc. In one example, focused application of energy at a neuromuscular junction facilitates neurotransmitter release at the neuromuscular junction without an upstream action potential. In one embodiment, contemplated targets for modulation may include portions of a pancreas responsible for controlling insulin release or portions of the liver responsible for sensing glucose/metabolites and/or regulating their circulating concentrations.

Assessment of Targeted Physiological Outcomes

The neuromodulation techniques discussed herein may be used to cause a targeted physiological outcome of a change in concentration (e.g., increased, decreased) of a molecule of interest and/or a change in characteristics of a molecule of interest. That is, the outcome may include selective modulation of one or more molecules of interest (e.g., a first molecule of interest, a second molecule of interest, and so on) and may refer to modulating or influencing a concentration (circulating, tissue) or characteristics (covalent modification) of a molecule as a result of energy application to one or more regions of interest (e.g., a first region of interest, a second region of interest, and so on) in one or more tissues (e.g., a first tissue, a second tissue, and so on). Modulation of a molecule of interest may include changes in characteristics of the molecule such as expression, secretion, translocation of proteins and direct activity changes based on ion channel effects either derived from the energy application itself or as a result of molecules directly effecting ion channels. Modulation of a molecule of interest may also refer to maintaining a desired concentration of the molecule, such that expected changes or fluctuations in concentration do not occur as a result of the neuromodulation. Modulation of a molecule of interest may refer to causing changes in molecule characteristics, such as enzyme-mediated covalent modification (changes in phosphorylation, aceylation, ribosylation, etc.). That is, it should be understood that selective modulation of a molecule of interest may refer to molecule concentration and/or molecule characteristics. The molecule of interest may be a biological molecule, such as one or more of carbohydrates (monosaccharaides, polysaccharides), lipids, nucleic acids (DNA, RNA), or proteins. In certain embodiments, the molecule of interest may be a signaling molecule such as a hormone (an amine hormone, a peptide hormone, or a steroid hormone), cytokine, or neurotransmitter.

The disclosed techniques may be used in assessment of patient condition as a result of the targeted physiological outcomes caused by neuromodulating treatment protocols. The disclosed techniques may use direct assessments of tissue condition or function as the targeted physiological outcomes. The assessment may occur before (i.e., baseline assessment), during, and/or after the neuromodulation. The assessment techniques may include at least one of functional magnetic resonance imaging, diffusion tensor magnetic resonance imaging, positive emission tomography, acoustic monitoring, thermal monitoring, or chemical sensing (e.g., immunochemical sensing). The assessment techniques may also include protein and/or molecule concentration assessment. The images from the assessment techniques may be received by the system for automatic or manual assessment. Based on the image data, the modulation parameters may also be modified. For example, a change in organ size or displacement may be utilized as a marker of local neurotransmitter concentration, and used as a surrogate marker for exposure of local cells to phenotype modulating neurotransmitters, and effectively as a marker of predicted effect on glucose metabolic pathways. The local concentration may refer to a concentration within a field of focus of the energy application.

Additionally or alternatively, the system may assess the presence or concentration of one or more molecules in the tissue or circulating in the blood. The concentration in the tissue may be referred to as a local concentration or resident concentration. Tissue may be acquired by a fine needle aspirate, and the assessment of the presence or levels of molecules of interest (e.g., metabolic molecules, markers of metabolic pathways, peptide transmitters, catecholamines) may be performed by any suitable technique known to one of ordinary skilled in the art.

In other embodiments, the targeted physiological outcomes may include, but are not limited to, tissue displacement, tissue size changes, a change in concentration of one or more molecules (either local, non-local, or circulating concentration), a change in gene or marker expression, afferent activity, and cell migration, etc. For example, tissue displacement (e.g., liver displacement) may occur as a result of energy application to the tissue. By assessing the tissue displacement (e.g., via imaging), other effects may be estimated. For example, a certain displacement may be characteristic of a particular change in molecule concentration. In one example, a 5% liver displacement may be indicative of or associated with a desired reduction in circulating glucose concentration based on empirical data. In another example, the tissue displacement may be assessed by comparing reference image data (tissue image before application of energy to the tissue) to post-treatment image data (tissue image taken after application of energy to the tissue) to determine a parameter of displacement. The parameter may be a maximum or average displacement value of the tissue. If the parameter of displacement is greater than a threshold displacement, the application of energy may be assessed as being likely to have caused the desired targeted physiological outcome.

In certain embodiments, the disclosed neuromodulation techniques may include a step of assessing the effect of the treatment protocols. For example, one or more direct or indirect assessments of a state of tissue function or condition may be used. In one embodiment, assessments may be performed before and after applying energy pulses to assess a change in molecule concentration as a result of the modulation. Further, the assessed characteristic or condition may be a value or an index, for example, a flow rate, a concentration, a cell population, or any combination thereof, which in turn may be analyzed by a suitable technique. For example, a relative change exceeding a threshold may be used to diagnose a patient. The diagnosis may be assessed via a measured clinical perturbation, such as a presence or absence of an increase in tissue structure size (e.g., lymph node size) or a change in concentration of one or more released molecules (e.g., relative to the baseline concentration before the neuromodulation). In one embodiment, the outcome may involve an increase in concentration above a threshold, e.g., above a about 50%, 100%, 200%, 400%, 1000% increase in concentration relative to baseline. The assessment may involve tracking a decrease in concentration of a molecule over time, e.g., at least a 10%, 20%, 30%, 50%, or 75% decrease in the molecule of interest. The increase or decrease or other induced and measurable effect may be measured within a certain time window from the start of a treatment, e.g., within about 5 minutes, within about 30 minutes.

Treatment of Clinical Conditions

As provided herein, the neuromodulation treatment protocols may be used as part of treatment for a clinical condition. Certain embodiments described herein provide neuromodulation techniques for the treatment of glucose metabolism and associated disorders. Glucose regulation is complex and involves different local and systemic metabolic pathways. Application of energy to targeted region/s of interest causes characteristic changes in these metabolic pathways that affect glucose regulation. In some embodiments, modulation at one or more regions of interest may be used to treat disorders including but not limited to, diabetes (i.e., type 1 or type 2 diabetes), hyperglycemia, sepsis, trauma, infection, physiological stress, diabetes-associated dementia, obesity, or other eating or metabolic disorders. In one example, physiological stress may be medically defined to include a variety of acute medical conditions (infection, severe injury/trauma, heart attack, bypass) as well as surgical instances with presentation of hyperglycemia.

In one example, the present techniques may be used to diagnose a subject with a metabolic disorder. The present techniques may also be used to diagnose and/or treat subjects with disorders of glucose regulation. Accordingly, the present techniques may be used to promote targeted physiological outcomes to changes concentration of a molecule of interest or to promote a desired circulating concentration or concentration range of one or more molecules of interest (e.g., glucose, insulin, glucagon, or a combination thereof). In one embodiment, the present techniques may be used to assess clinical conditions associated with circulating (i.e., blood) glucose levels. In one embodiment, the treatment protocols may be used to treat patients with blood glucose levels outside of normal. In another embodiment, the treatment protocols may be used to maintain desired normal glucose levels. Glucose levels may be categorized as follows:

Fasted:

Less than 50 mg/dL (2.8 mmol/L): Insulin Shock 50-70 mg/dL (2.8-3.9 mmol/L): low blood sugar/hypoglycemia 70-110 mg/dL (3.9-6.1 mmol/L): normal 110-125 mg/dL (6.1-6.9 mmol/L): elevated/impaired (pre-diabetic)

125 (7 mmol/L): diabetic

Non-fasted (postprandial approximately 2 hours after meal):

70-140 mg/dL: Normal 140-199 mg/dL (8-11 mmol/L): Elevated or "borderline"/ prediabetes More than 200 mg/dL: (11 mmol/L): Diabetes In another example, as provided herein, neuromodulation of lymphatic tissue may result in altered immune activity or function. In certain embodiments, neuromodulation of a lymph node results in local enlargement of the lymph node relative to a contralateral lymph node. The enlargement, or hypertrophy, may be associated with a change in perilymphatic vessel muscle cell tone, longer term recruitment and re-organization of lymphatic vessels around the lymph node, and/or molecular changes at key barrier tissues (such as high endothelial venules (HEV) within the lymph node) including alteration of important transport proteins (such as aquaporin (water/liquid transport), or CCL21/CXCL13 secretion (cell chemokines)). The outcomes may result in shifts in cell densities, cell counts, and the overall lymph node tissue environment, including the enlargement. Further, activation of the lymph node may result in an activation chain that expands or amplifies the local activation to systemically activate the lymphatic system. That is, local stimulation may result in downstream and upstream activation of lymphatic systems. Accordingly, local changes may be used to activate a systemic immune response. Additional changes may include alteration of lymphatic fluid flow, immune cell trafficking into/out of the lymphatic tissue, alteration of immune cell phenotype or local immune response, and/or antigen trafficking into/out of the lymphatic tissue. Local stimulation may enable tissue or location specific increase in lymphatic fluid or immune cell recruitment. Accordingly, neuromodulation may be used to treat immune conditions by changing activity and/or function of immune pathways.

While certain embodiments are disclosed in the context of ultrasound energy application, it should be understood that other energy types are contemplated, e.g., magnetic resonance or radiofrequency applied above the skin. Also, high power EIT is also contemplated, where a grid of electrodes steer electrical current fields regionally within the body to the target area.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A neuromodulation system, comprising:

a noninvasive ultrasound probe configured to apply nonablative ultrasound energy to a region of interest in a patient's body, the noninvasive ultrasound probe comprising an ultrasound therapy transducer and an ultrasound imaging transducer; and a controller configured to:

access a prior ultrasound image associated with a predetermined treatment position and orientation of the noninvasive ultrasound probe, wherein the predetermined treatment position and orientation corresponds to a location of a surface marking on the patient's body;

acquire ultrasound image data of the region of interest using the ultrasound imaging transducer;

identify one or more anatomical features within the region of interest based on the ultrasound image data;

determine that the noninvasive ultrasound probe is aligned with the predetermined treatment position and orientation based on the ultrasound image data and the prior ultrasound image associated with the predetermined treatment position and orientation of the noninvasive ultrasound probe; and control application of the nonablative ultrasound energy to activate axon terminals of one or more nerve pathways in the region of interest via the noninvasive ultrasound probe responsive to determining that the noninvasive ultrasound probe is aligned with the predetermined treatment position and orientation, wherein the activation of the one or more nerve pathways causes a change in concentration of a circulating molecule.

2. The neuromodulation system of claim 1, wherein the controller is configured to cause display of an indication related to determining that the noninvasive ultrasound probe is aligned with the predetermined treatment position and orientation.

3. The neuromodulation system of claim 1, wherein the controller is configured to transmit instructions to an actuator of the noninvasive ultrasound probe responsive to determining that the noninvasive ultrasound probe is aligned with the predetermined treatment position and orientation.

4. The neuromodulation system of claim 1, wherein the controller is configured to transmit instructions to activate a light responsive to determining that the noninvasive ultrasound probe is aligned with the predetermined treatment position and orientation.

5. The neuromodulation system of claim 1, wherein the controller is configured to:

receive updated image data from the ultrasound imaging transducer associated with a different position and orientation on the patient's body;

determine that the noninvasive ultrasound probe is not aligned with the predetermined treatment position and orientation based on the updated image data and the prior ultrasound image associated with the predetermined treatment position and orientation of the noninvasive ultrasound probe; and stop application of the nonablative ultrasound energy via the noninvasive ultrasound probe responsive to determining that the updated image data is not aligned with the predetermined treatment position and orientation.

6. The neuromodulation system of claim 5, wherein the controller is configured to transmit instructions to an actuator of the noninvasive ultrasound probe responsive to determining that the noninvasive ultrasound probe is not aligned with the predetermined treatment position and orientation.

7. The neuromodulation system of claim 5, wherein the controller is configured to provide an indication of a position and orientation of the noninvasive ultrasound probe relative to the predetermined treatment position and orientation based on the updated image data.

8. The neuromodulation system of claim 1, wherein the controller is configured to determine that the noninvasive ultrasound probe is aligned with the predetermined treatment position and orientation for a period of time before controlling the application of the nonablative ultrasound energy.

9. The neuromodulation system of claim 1, wherein the controller is configured to determine that the noninvasive ultrasound probe is aligned with the predetermined treatment position and orientation based on an image registration or alignment of the ultrasound image data and the prior ultrasound image associated with the predetermined treatment position and orientation of the noninvasive ultrasound probe.

10. The neuromodulation system of claim 1, wherein the region of interest is a liver or sub-region of the liver of the patient.

11. The neuromodulation system of claim 10, wherein the nonablative ultrasound energy applied to the liver or sub-region of the liver causes a change in concentration of circulating glucose.

12. The neuromodulation system of claim 1, wherein the region of interest is a liver or a sub-region of the liver, or suborgans of a gastrointestinal tract.

13. The neuromodulation system of claim 1, wherein the region of interest is a liver or a sub-region of the liver, and suborgans of a gastrointestinal tract.

14. The neuromodulation system of claim 1, wherein the circulating molecule comprises glucose.

15. The neuromodulation system of claim 1, wherein the nonablative ultrasound energy comprises a temporal average intensity less than 35 W/cm$^2$.

16. A neuromodulation system, comprising:
a noninvasive ultrasound probe configured to apply nonablative ultrasound energy to activate axon terminals of one or more nerve pathways in a region of interest in a patient's body such that activation of the one or more nerve pathways causes a change in concentration of a circulating molecule, the noninvasive ultrasound probe comprising:
an ultrasound therapy transducer;
an ultrasound imaging transducer; and
a haptic device; and
a controller configured to:
receive ultrasound image data from the ultrasound imaging transducer from a plurality of positions and/or orientations of the noninvasive ultrasound probe on the patient's body;

identify one or more anatomical features within a region of interest based on the ultrasound image data;

identify one or more aligned positions and/or orientations of the plurality that are aligned with a predetermined treatment position and orientation of the noninvasive ultrasound probe based on the ultrasound image data, wherein the predetermined treatment position and orientation corresponds to a location of a surface marking on the patient's body;

transmit instructions to activate the haptic device of the noninvasive ultrasound probe in a first operating mode while the noninvasive ultrasound prove in a first operating mode while the noninvasive ultrasound probe is at one of the one or more aligned positions and/or orientations; and transmit instructions to active the haptic device of the noninvasive ultrasound probe in a second operating mode while the noninvasive ultrasound probe is not one of the one or more aligned positions and/or orientations.

17. The neuromodulation system claim 16, wherein the controller is further configured to transmit instructions to activate audio or display guidance while the noninvasive ultrasound probe is not at the one or more aligned positions and/or orientations, wherein the audio or display guidance comprises a direction of movement toward one of the one or more aligned positions and/or orientations.

18. The neuromodulation system of claim 16, wherein the first operating mode comprise a first vibration pattern and the second operating mode comprises a second vibration pattern different than the first vibration pattern.

19. A method for treating a patient with a metabolic disorder using a noninvasive ultrasound probe comprising an ultrasound therapy transducer and an ultrasound imaging transducer, comprising:
accessing a prior ultrasound image associated with a predetermined treatment position and orientation of the noninvasive ultrasound probe, wherein the predetermined treatment position and orientation corresponds to a location of a surface marking on the patient's body;
acquiring ultrasound image data from the ultrasound imaging transducer associated with a position and orientation of the noninvasive ultrasound probe on the patient's body;
identifying one or more anatomical features within a region of interest based on the ultrasound image data;
determining that the noninvasive ultrasound probe is aligned with the predetermined treatment position and orientation based on the ultrasound image data and the prior ultrasound image associated with the predetermined treatment position and orientation of the noninvasive ultrasound probe; and
controlling application of a nonablative ultrasound energy to activate axon terminals of one or more nerve pathways in the region of interest via the noninvasive ultrasound probe responsive to determining that the noninvasive ultrasound probe is aligned with the predetermined treatment position and orientation, wherein the activation of the one or more nerve pathways causes a change in concentration of a circulating molecule.

20. The method of claim 19, further comprising providing feedback in response to determining that the noninvasive ultrasound probe is not aligned with the predetermined treatment position and orientation.

* * * * *